United States Patent
Olafsson et al.

(10) Patent No.: US 8,992,630 B2
(45) Date of Patent: Mar. 31, 2015

(54) METHOD AND APPARATUS FOR DECREASING BUILD HEIGHT OF PROSTHETIC PRODUCTS

(75) Inventors: Sigurdur Olafsson, Reykjavik (IS); Helgi Jonsson, Reykjavik (IS)

(73) Assignee: Össur hf, Reykjavik (IS)

( * ) Notice: Subject to any disclaimer, the term of this patent is extended or adjusted under 35 U.S.C. 154(b) by 0 days.

(21) Appl. No.: 13/480,193

(22) Filed: May 24, 2012

(65) Prior Publication Data
US 2012/0232676 A1 Sep. 13, 2012

Related U.S. Application Data

(62) Division of application No. 12/441,239, filed as application No. PCT/US2007/007855 on Sep. 14, 2007, now Pat. No. 8,192,503.

(60) Provisional application No. 60/844,871, filed on Sep. 15, 2006.

(51) Int. Cl.
*A61F 2/80* (2006.01)
*A61F 2/76* (2006.01)
*A61F 2/78* (2006.01)
*A61F 2/30* (2006.01)
*A61F 2/50* (2006.01)

(52) U.S. Cl.
CPC ... *A61F 2/76* (2013.01); *A61F 2/78* (2013.01); *A61F 2002/30359* (2013.01); *A61F 2002/30433* (2013.01); *A61F 2002/5083* (2013.01); *A61F 2220/0033* (2013.01); *A61F 2220/0041* (2013.01)

USPC .............................................. 623/38

(58) Field of Classification Search
USPC ....................................... 623/32–38
See application file for complete search history.

(56) References Cited

U.S. PATENT DOCUMENTS

| | | | |
|---|---|---|---|
| 1,302,336 A | 4/1919 | Erickson | |
| 3,906,552 A | 9/1975 | Weber | |
| 4,564,365 A | 1/1986 | Winer et al. | |
| 5,529,576 A | 6/1996 | Lundt et al. | |
| 5,746,772 A * | 5/1998 | Jacobs | 623/35 |
| 5,746,774 A | 5/1998 | Kramer et al. | |
| 6,991,658 B2 | 1/2006 | Slemker et al. | |

(Continued)

FOREIGN PATENT DOCUMENTS

| | | |
|---|---|---|
| DE | 3937379 | 5/1991 |
| WO | WO 98/38951 | 9/1998 |

(Continued)

OTHER PUBLICATIONS

International Search Report and Written Opinion for International Application No. PCT/US2007/078558, dated Mar. 6, 2008.

(Continued)

*Primary Examiner* — Bruce E Snow
(74) *Attorney, Agent, or Firm* — Knobbe, Martens, Olson & Bear, LLP.

(57) ABSTRACT

An adapter assembly allows mechanical coupling of prosthetic components such that a distal end of a socket adapter extends below a top surface of a prosthetic. The adapter assembly may include sets of external threads to operatively engage internally threaded surfaces of the prosthetic and the socket adapter.

22 Claims, 15 Drawing Sheets

(56) References Cited

U.S. PATENT DOCUMENTS

2004/0204770 A1    10/2004    Curtis
2005/0089363 A1    4/2005    Curtis
2005/0171617 A1    8/2005    Curtis

FOREIGN PATENT DOCUMENTS

WO    WO 99-16391    4/1999
WO    WO 03-096940    11/2003

OTHER PUBLICATIONS

International Preliminary Report on Patentability for International Application No. PCT/US2007/078558, dated Mar. 26, 2009.
European Office Action for application 07842544.4-1526 dated Sep. 17, 2010.
Mar. 21, 2011 First Office Action for Chinese Application No. 200780042120.6 filed on Sep. 14, 2007.
Mar. 31, 2012 Second Office Action for Chinese Application No. 200780042120.6 filed on Sep. 14, 2007.

* cited by examiner

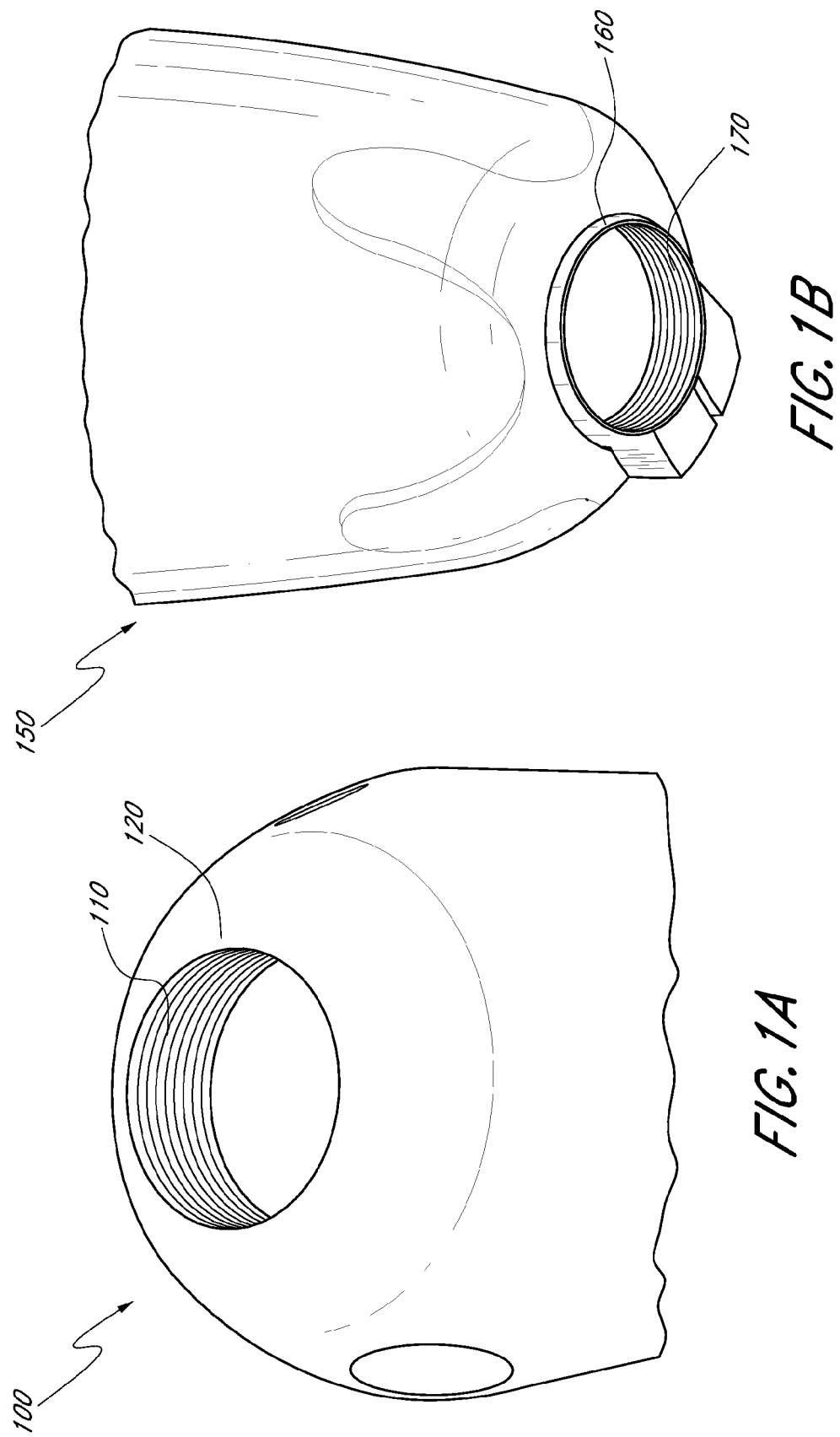

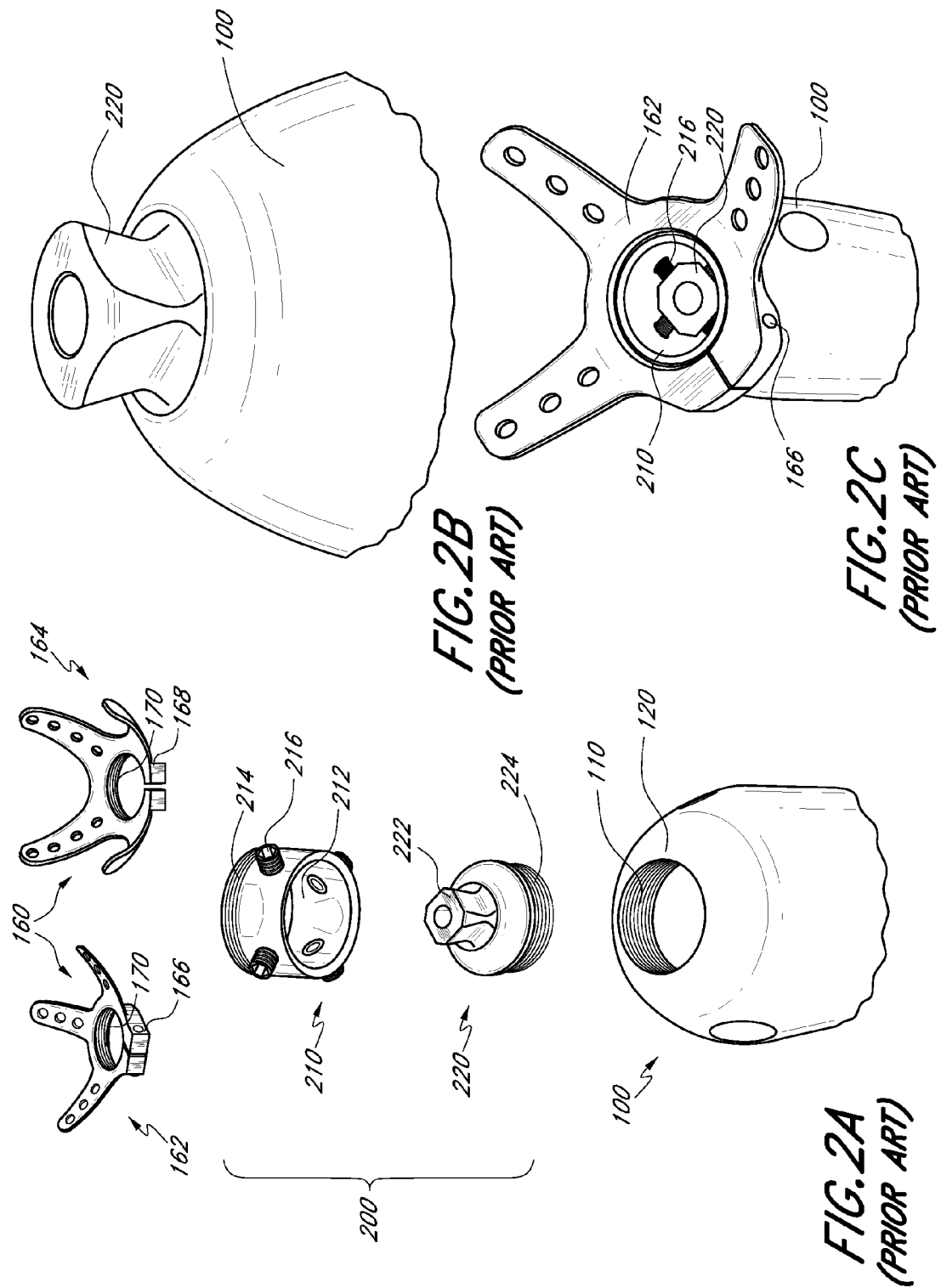

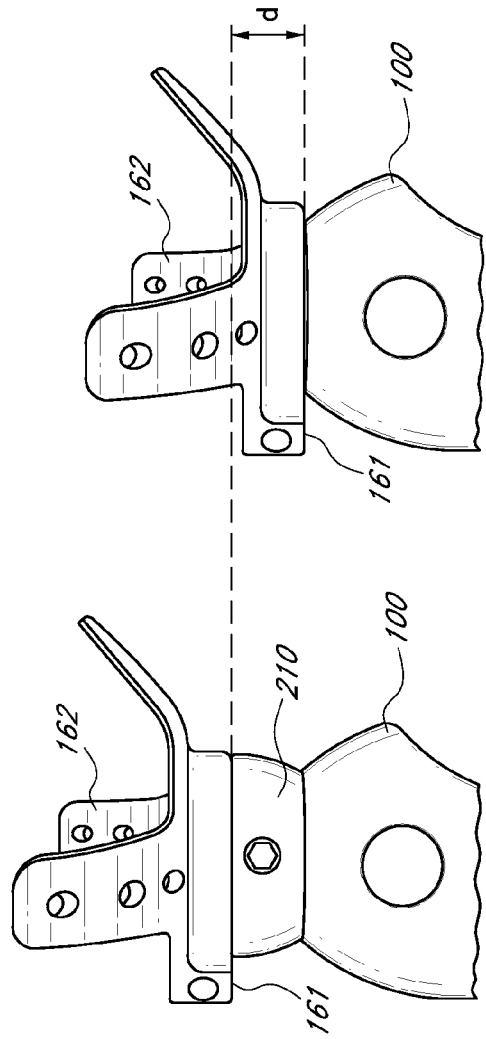
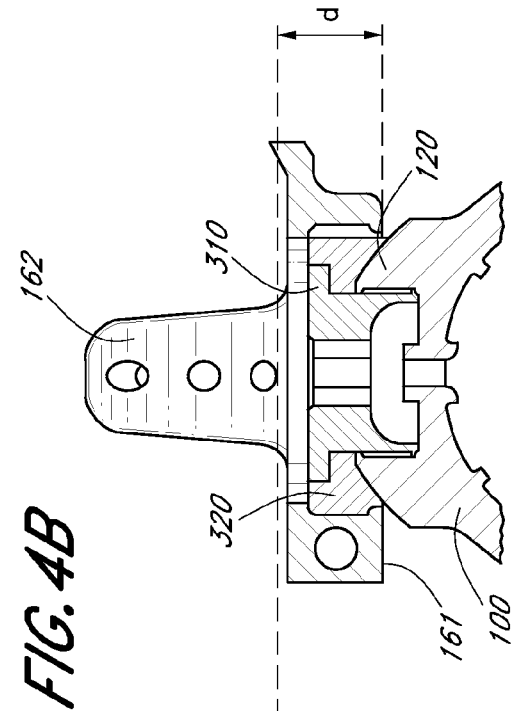
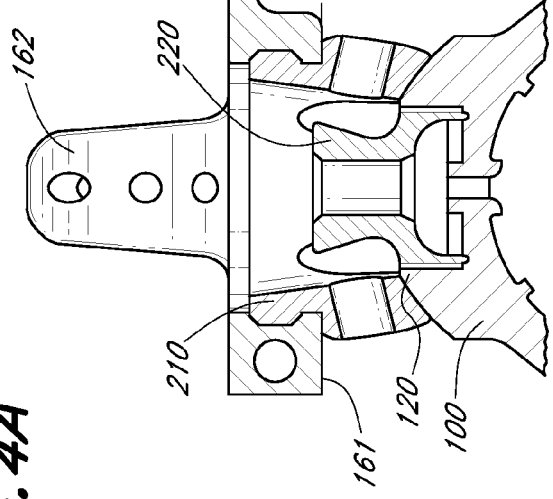
FIG.4A (PRIOR ART)
FIG.4B

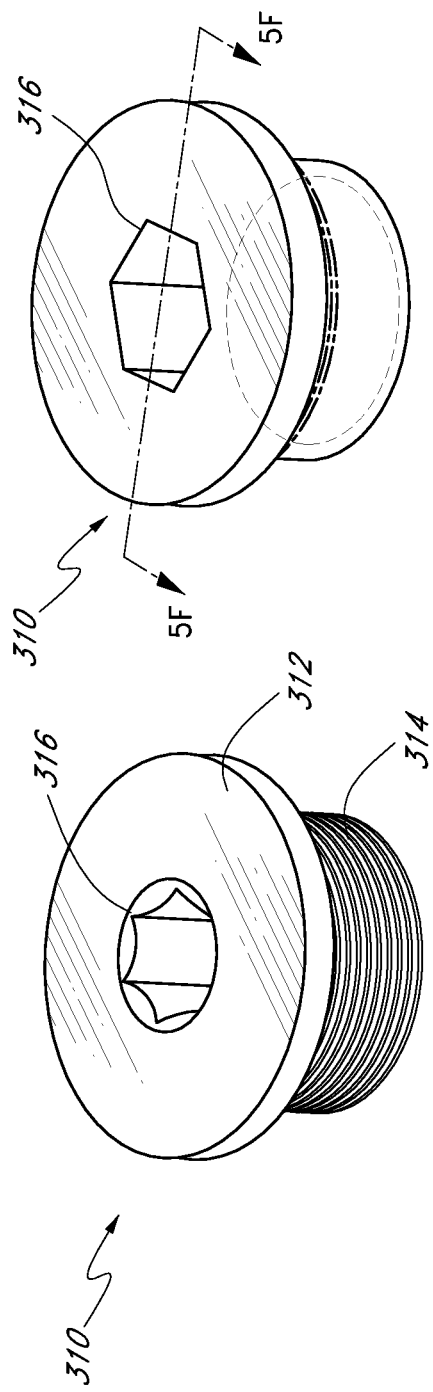
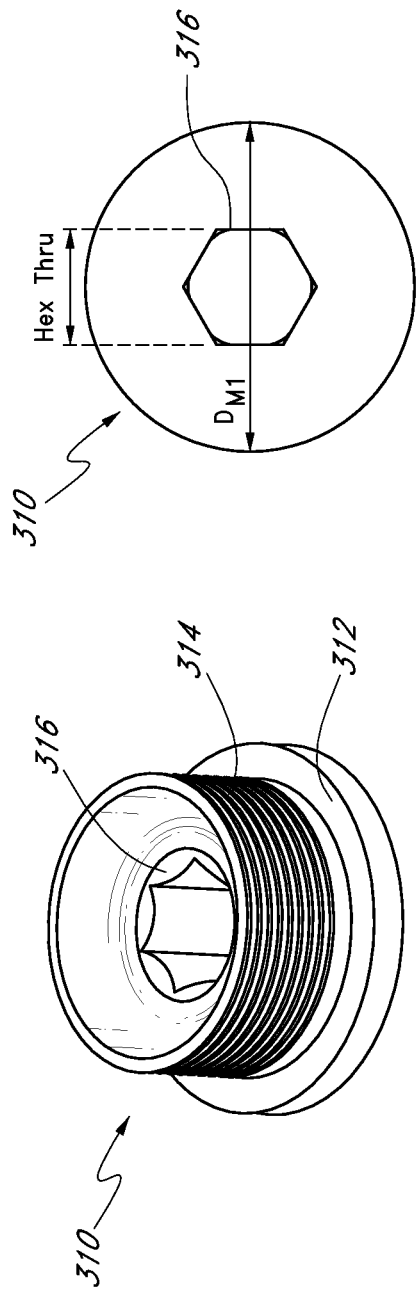
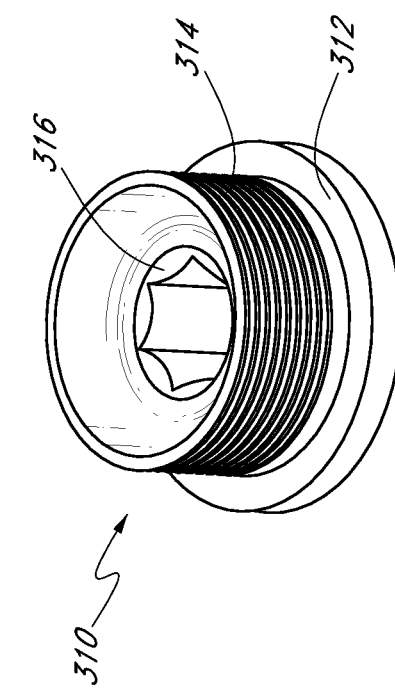
FIG.5A
FIG.5B
FIG.5C
FIG.5D

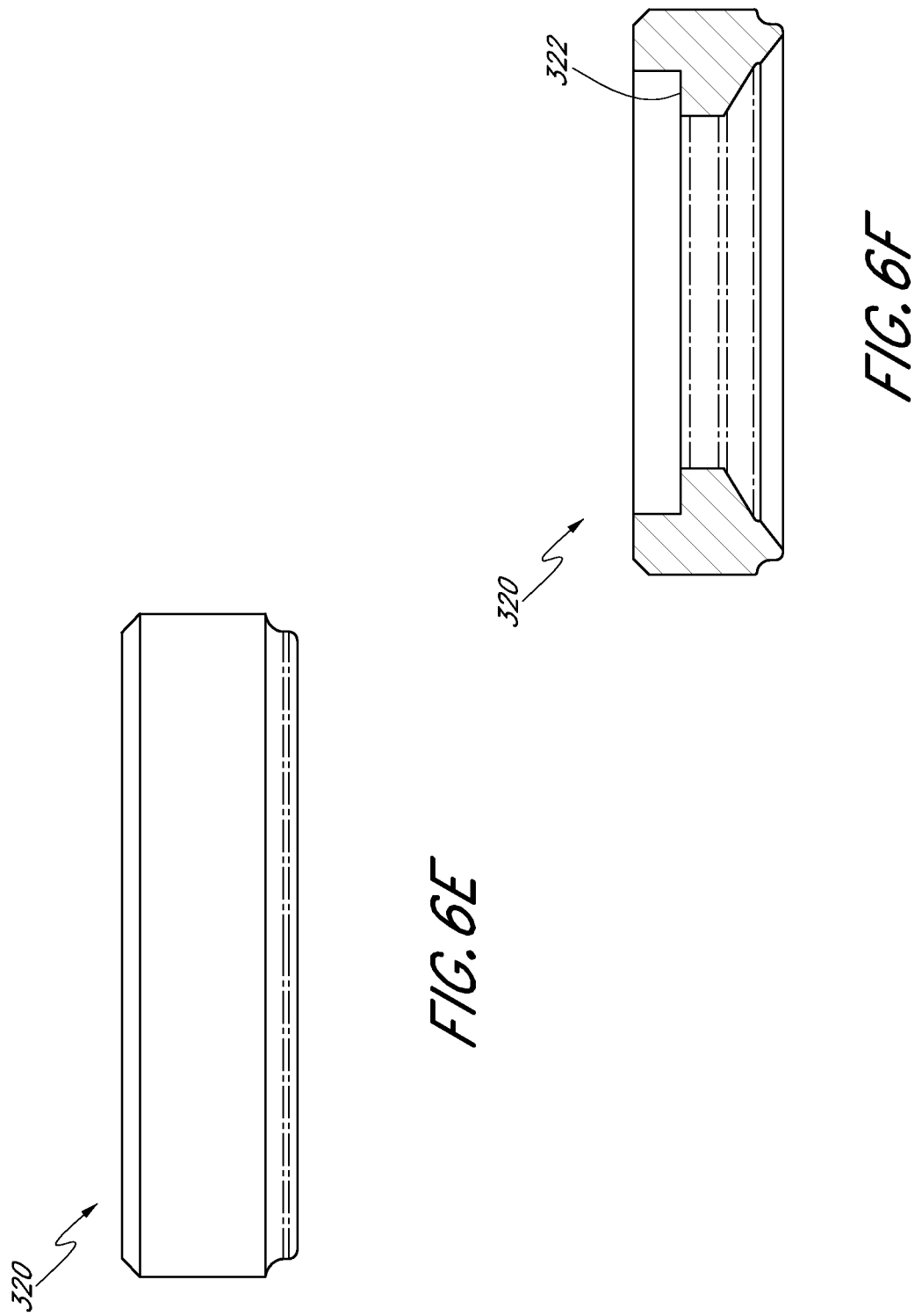

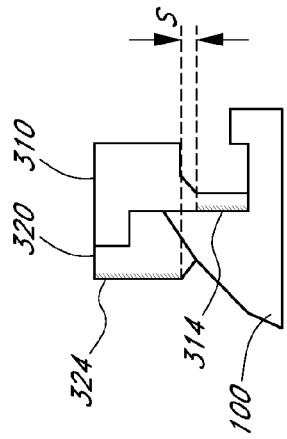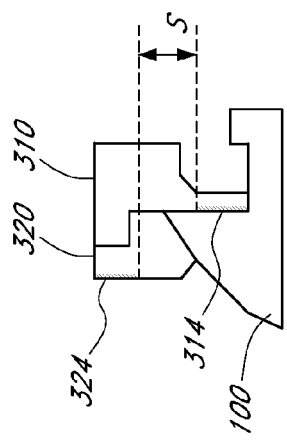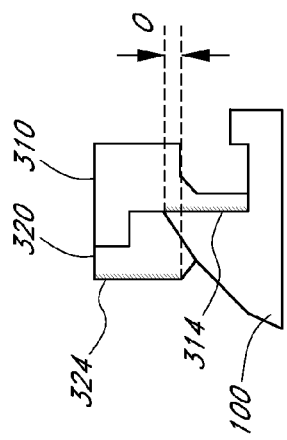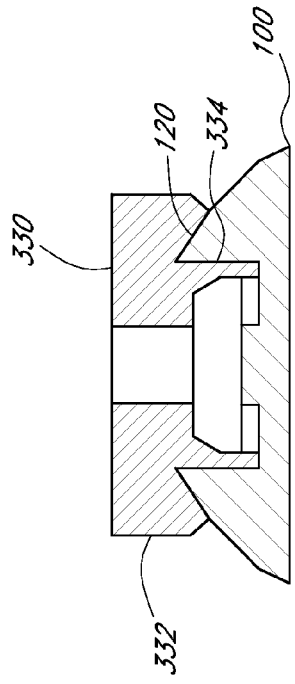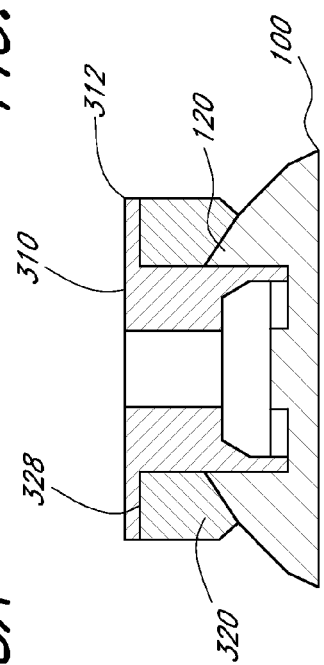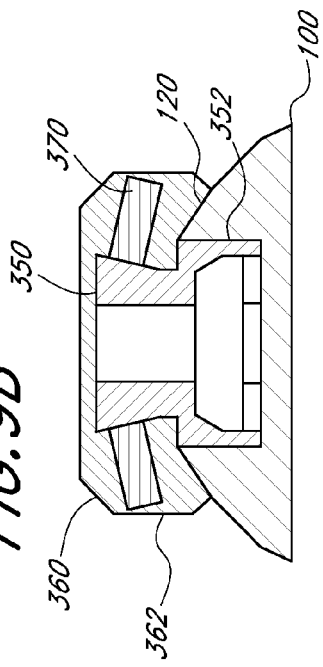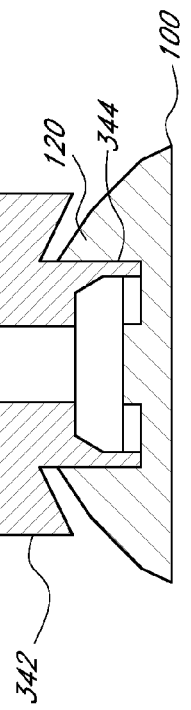

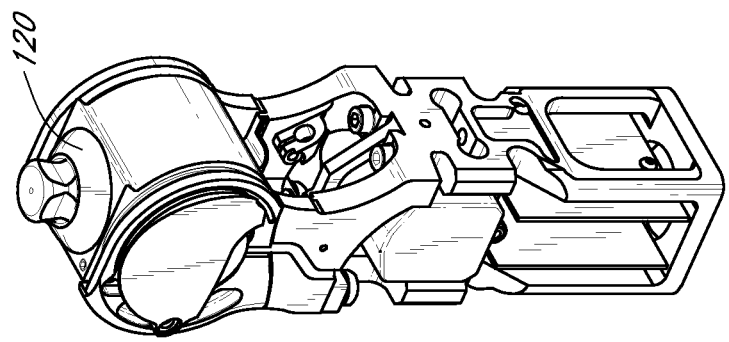
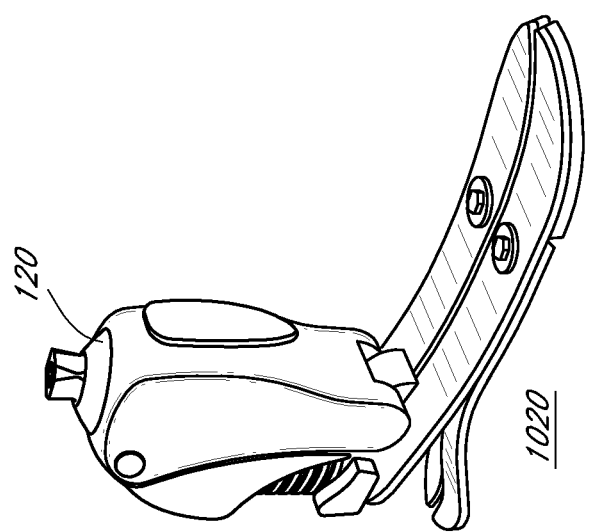
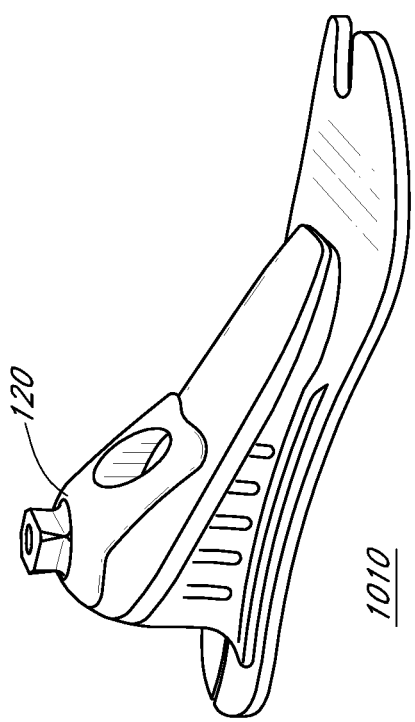
FIG. 10A

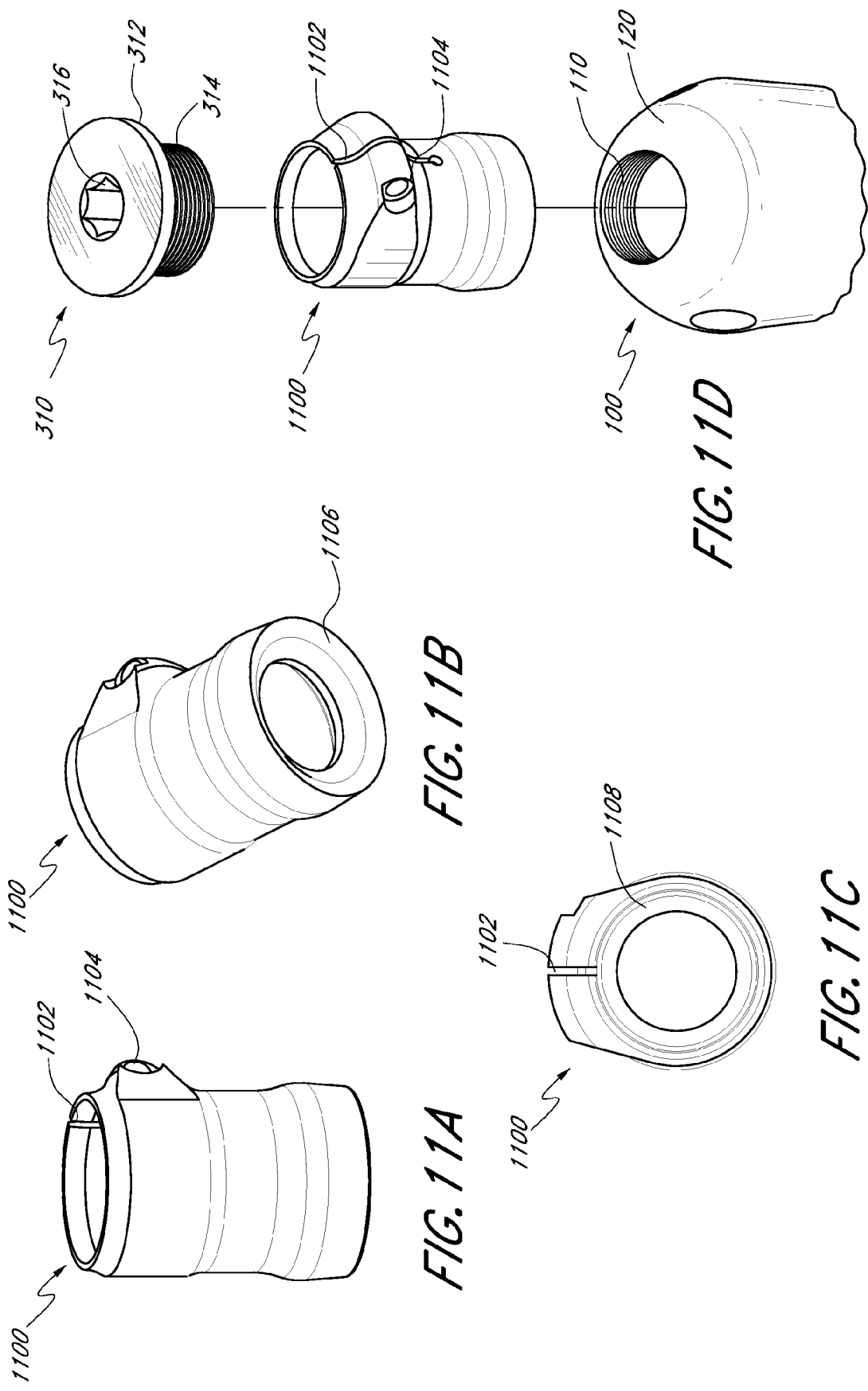

METHOD AND APPARATUS FOR DECREASING BUILD HEIGHT OF PROSTHETIC PRODUCTS

RELATED APPLICATIONS

This application is a divisional application of U.S. application Ser. No. 12/441,239, entitled "METHOD AND APPARATUS FOR DECREASING BUILD HEIGHT OF PROSTHETIC PRODUCTS," filed on Mar. 13, 2009, which is a national phase filing of PCT Patent Application No. PCT/US2007/078558, filed Sep. 14, 2007, which claims a priority benefit to U.S. Provisional Patent Application Ser. No. 60/844,871, filed Sep. 15, 2006, each of which is incorporated herein by reference in its entirety.

BACKGROUND

1. Field

Embodiments of the invention relate to prosthetic products, and more particularly to systems and methods for decreasing build height of prosthetic products.

2. Description of the Related Art

Millions of individuals worldwide rely on prosthetic and/or orthotic devices to compensate for disabilities, such as amputation or debilitation, and to assist in the rehabilitation of injured limbs. Orthotic devices include external apparatuses used to support, align, prevent, protect, correct deformities of, or improve the function of movable parts of the body. Prosthetic devices include apparatuses used as artificial substitutes for a missing body part, such as an arm or leg.

SUMMARY

Embodiments of the present invention include, but are not limited to, adapters for connecting parts, systems incorporating the adapters, and/or methods for assembling the systems. The adapters may be used to attach prosthetic products, but can have other uses as well, such as with orthotic products.

In certain embodiments, a system for mechanically coupling prosthetic components comprises a prosthetic, a socket adapter, and an adapter assembly. The prosthetic includes a top surface. The socket adapter includes a distal end. The adapter assembly is in fixed mechanical communication with the prosthetic and the socket adapter. The distal end of the socket adapter extends below the top surface of the prosthetic. A method of mechanically coupling the prosthetic components includes engaging the prosthetic and the socket adapter such that the distal end of the socket adapter is fixed below the top surface of the prosthetic.

In certain embodiments, a system for mechanically coupling prosthetic components comprises a prosthetic, a socket adapter, and an adapter assembly. The prosthetic includes a top surface and an internally threaded surface recessed within the top surface. The socket adapter includes an internally threaded surface at a distal end. The adapter assembly has a top end and a bottom end. The adapter assembly comprises a first externally threaded surface configured to operatively engage the internally threaded surface of the prosthetic and a second externally threaded surface configured to operatively engage the internally threaded surface at the distal end of the socket adapter. The second externally threaded surface extends below the top surface of the prosthetic when the adapter assembly is coupled to the prosthetic. A method of mechanically coupling the prosthetic components includes engaging the first externally threaded surface to the internally threaded surface of the prosthetic and engaging the second externally threaded surface to the internally threaded surface of the socket adapter.

In certain embodiments, a system for mechanically coupling prosthetic components comprises a prosthetic, a socket adapter, and an adapter assembly. The prosthetic includes a top surface and an internally threaded surface recessed within the top surface. The socket adapter includes an internally threaded surface at a distal end. The adapter assembly has a top end and a bottom end. The adapter assembly comprises a first externally threaded surface configured to operatively engage the internally threaded surface of the prosthetic and a second externally threaded surface configured to operatively engage the internally threaded surface at the distal end of the socket adapter. The distal end of the socket adapter extends below the top surface of the prosthetic when the system is assembled. A method of mechanically coupling the prosthetic components includes engaging the first externally threaded surface to the internally threaded surface of the prosthetic and engaging the second externally threaded surface to the internally threaded surface of the socket adapter.

In certain embodiments, a system for mechanically coupling prosthetic components comprises a prosthetic, a socket adapter, and an adapter assembly. The prosthetic includes a top surface and an internally threaded surface recessed within the top surface. The socket adapter includes an internally threaded surface at a distal end. The adapter assembly comprises a female element and a male element. The female element includes exterior threads to operatively engage the internally threaded surface at the distal end of the socket adapter. The male element includes exterior threads to operatively engage the internally threaded surface of the prosthetic. The male element further includes a lip adapted to compress the female element against the top surface of the prosthetic. A method of mechanically coupling the prosthetic components includes extending the male element through the female element and into the recessed surface of the prosthetic, engaging the exterior threads of the male element to the internally threaded surface of the prosthetic, and engaging the exterior threads of the female element to the internally threaded surface of the socket adapter.

In certain embodiments, a system for mechanically coupling prosthetic components comprises a prosthetic, a socket adapter, and an adapter assembly. The prosthetic includes a top surface and an internally threaded surface recessed within the top surface. The socket adapter includes an internally threaded surface at a distal end. The internally threaded surface of the socket adapter defines a socket adapter cavity. The adapter assembly comprises a female element and a male element. The female element includes exterior threads to operatively engage the internally threaded surface at the distal end of the socket adapter. The male element includes exterior threads to operatively engage the internally threaded surface of the prosthetic. The male element is substantially inside the socket adapter cavity when the adapter assembly is coupled to the prosthetic. A method of mechanically coupling the prosthetic components includes extending the male element through the female element and into the recessed surface of the prosthetic, engaging the exterior threads of the male element to the internally threaded surface of the prosthetic, and engaging the exterior threads of the female element to the internally threaded surface of the socket adapter.

In certain embodiments, a system for mechanically coupling prosthetic components comprises a prosthetic, a socket adapter, and an adapter assembly. The prosthetic includes a top surface and an internally threaded surface recessed within the top surface. The socket adapter includes an internally threaded surface at a distal end and a plurality of generally longitudinally extending prongs. The adapter assembly comprises a female element and a male element. The female element includes exterior threads to operatively engage the internally threaded surface at the distal end of the socket adapter. The male element includes exterior threads to operatively engage the internally threaded surface of the prosthetic. The plurality of prongs extend below a top of the male element. A method of mechanically coupling the prosthetic components includes extending the male element through the female element and into the recessed surface of the prosthetic, engaging the exterior threads of the male element to the internally threaded surface of the prosthetic, and engaging the exterior threads of the female element to the internally threaded surface of the socket adapter.

In certain embodiments, a system for mechanically coupling prosthetic components comprises a prosthetic, a socket adapter, and an adapter assembly. The prosthetic includes a top surface and an internally threaded surface recessed within the top surface. The socket adapter includes an internally threaded surface at a distal end. The internally threaded surface of the socket adapter has a larger diameter than the internally threaded surface of the prosthetic. The adapter assembly comprises a female element and a male element. The female element is generally hollow and generally cylindrical. The female element includes an outer surface having exterior threads to operatively engage the internally threaded surface at the distal end of the socket adapter, an upper portion including a lip projecting inwardly from an interior surface, and a lower portion including a concave surface to conformally engage the rounded top surface of the prosthetic. The male element is generally cylindrical. The male element includes an outer surface having exterior threads to operatively engage the internally threaded surface of the prosthetic, a substantially flat upper portion including a lip projecting outwardly from the outer surface and adapted to engage the lip of the female element and to compress the lower portion of the female element against the rounded top surface of the prosthetic. The exterior threads of the male element fit through the lip of the female element. A method of mechanically coupling the prosthetic components includes extending the male element through the female element and into the recessed surface of the prosthetic, engaging the exterior threads of the male element to the internally threaded surface of the prosthetic, and engaging the exterior threads of the female element to the internally threaded surface of the socket adapter.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught or suggested herein without necessarily achieving other objects or advantages as may be taught or suggested herein.

All of these embodiments are intended to be within the scope of the invention herein disclosed. These and other embodiments will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

These and other features, aspects, and advantages of the invention disclosed herein are described below with reference to the drawings of preferred embodiments, which are intended to illustrate and not to limit the invention.

FIG. 1A is a top perspective view of an example of a prosthetic.

FIG. 1B is a bottom perspective view of an example socket.

FIG. 2A depicts perspective views of a plurality of adapters that may be used to mechanically couple a prosthetic and a socket.

FIG. 2B is a perspective view of partial assembly of the elements of FIG. 2A.

FIG. 2C is a perspective view of further assembly of the elements of FIG. 2A.

FIG. 4A is a side perspective view of the assembled systems of FIGS. 2A and 3A shown side-by-side.

FIG. 4B is a cut-away view of the assembled systems of FIGS. 2A and 3A shown side-by-side.

FIG. 5A is a top perspective view of a male element of an example adapter.

FIG. 5B is a schematic top perspective view of the male element of FIG. 5A.

FIG. 5C is a bottom perspective view of the male element of FIG. 5A.

FIG. 5D is a schematic top plan view of the male element of FIG. 5A.

FIG. 6E is a schematic side plan view of the female element of FIG. 6A.

FIG. 6F is a schematic cross-sectional view of the female element of FIG. 6A taken along the line 6F-6F in FIG. 6B.

FIG. 8A is a cross-sectional schematic view of a portion of an embodiment of an adapter system.

FIG. 8B is a cross-sectional schematic view of a portion of another embodiment of an adapter system.

FIG. 8C is a cross-sectional schematic view of a portion of yet another embodiment of an adapter system.

FIG. 9A is a cross-sectional schematic view of another example adapter.

FIG. 9B is a cross-sectional schematic view of yet another example adapter.

FIG. 9C is a cross-sectional schematic view of still another example adapter.

FIG. 9D is a cross-sectional schematic view of yet still another example adapter.

FIG. 10A is a perspective view of a plurality of example prosthetics.

FIG. 11A is a top perspective view of another female element of an example adapter.

FIG. 11B is a bottom perspective view of the female element of FIG. 11A.

FIG. 11C is a top plan view of the female element of FIG. 11A.

FIG. 11D is a perspective view of partial assembly of the female element of FIG. 11A with the male element of FIG. 5A and the prosthetic of FIG. 1A.

DETAILED DESCRIPTION OF THE PREFERRED EMBODIMENTS

Figure 3B:
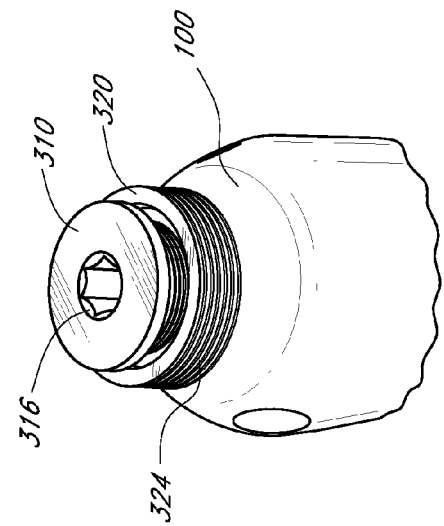
FIG. 3B is a perspective view of partial assembly of the elements of FIG. 3A.

Although certain preferred embodiments and examples are disclosed below, it will be understood by those in the art that the invention extends beyond the specifically disclosed embodiments and/or uses of the invention and obvious modifications and equivalents thereof. Thus, it is intended that the scope of the invention herein disclosed should not be limited by the particular disclosed embodiments described below.

Some preferred embodiments of the invention described herein relate generally to prosthetic and orthotic systems and, in particular, to prosthetic and orthotic devices having a low build height. While the description sets forth various embodiment-specific details, it will be appreciated that the description is illustrative only and should not be construed in any way as limiting the invention. Furthermore, various applications of the invention, and modifications thereto, which may occur to those who are skilled in the art, are also encompassed by the general concepts described herein.

The terms "prosthetic" and "prosthesis" as used herein are broad terms and are used in their ordinary sense and refer to, without limitation, any system, device, or apparatus that may be used as an artificial substitute or support for a body part.

The term "socket" as used herein is a broad term and is used in its ordinary sense and refers to, without limitation, any system, device, or apparatus that may be used to couple a body part to a device or apparatus, and in one embodiment, the part of the prosthesis that fits around the residual limb.

The term "adapter" as used herein is a broad term and is used in its ordinary sense and refers to, without limitation, any system, device, or apparatus that may be used to couple a prosthetic or orthotic directly or indirectly to a socket.

FIGS. 1A and 1B illustrate examples of prosthetics and sockets that may to be mechanically coupled to form a replacement limb. FIG. 1A is a top perspective view of an example embodiment of a prosthetic 100 comprising a recessed portion having interior threads 110 and a top surface 120. In certain embodiments, the top surface 120 of the prosthetic 100 has a domed top surface 120. FIG. 1B illustrates a bottom perspective view of an example embodiment of a socket 150 configured to be coupled to the prosthetic 100. The socket 150 includes a cylindrical body having a closed end adapted to receive an amputee's limb, such as the stump of an amputated leg. Available sockets include Iceross® and Icex® from Össur hf of Reykjavik, Iceland. Sockets from other manufacturers are also possible.

The socket 150 may comprise a socket adapter 160, for example a "three-prong" or a "four-prong" adapter described below, which may be fused or otherwise attached to the main body of the socket 150 at its distal end and which includes interior threads 170. Coupling of the prosthetic 100 and the socket 150 in some embodiments thus requires an adapter in order to couple the interior threads 110 of the prosthetic 100 to the interior threads 170 of the socket 150. The prosthetic 100 forms part of a prosthetic knee (for trans-femoral users); however, the systems, adapters, and methods described herein may also be applied to other prosthetics or other devices, such as prosthetic ankles (trans-tibial users), prosthetic feet, elbows (trans-ulnal users), shoulders, and the like (see FIG. 10A). It will also be appreciated that other embodiments may include different connection mechanisms other than the interior threads 110 of the prosthetic 100 and the interior threads 170 of the socket adapter 160, for example, exterior threads, clamps, snap-fitting, mechanical interlocks, adhesives, press-fit, etc.

FIG. 2A depicts perspective views of a plurality of adapters that may be used to mechanically couple the prosthetic 100 and the socket 150. As described above, the socket 150 may include a socket adapter 160 having interior threads 170. In FIG. 2A, two possibilities for the adapter 160 of FIG. 1B are depicted: the adapter 162 is a "three-prong" adapter and the adapter 164 is a "four-prong" adapter. The "prongs" comprise elements that extend generally longitudinally from the threaded base of the adapter 160. It will be appreciated that any suitable number of prongs may be used, as well as any shape (e.g., hemispherical) that can suitably engage the main body of the socket 150.

An adapter system for mechanically coupling the prosthetic 100 to the socket 150 in FIG. 2A comprises an adapter assembly 200 including two adapters, a male pyramid 220 and a female pyramid 210. The male pyramid 220 comprises a frusto-pyramidal portion 222 that is inverted with respect to a main body having at least a portion comprising exterior threads 224, which, for example, are configured to engage the interior threads 110 of the prosthetic 100. FIG. 2B illustrates the adapter 220 mechanically coupled (e.g., screwed into) the prosthetic 100.

Although the adapter 220 in FIG. 2B is slightly different than the adapter 220 illustrated in FIG. 2A, it will be appreciated that any suitable adapter with an inverted frusto-pyramidal portion 222 and exterior threads 224 may be used, depending on the configuration of the prosthetic 100. For example, if the recessed portion of the prosthetic 100 has a large diameter, the adapter 220 may have a top surface between the inverted frusto-pyramidal portion 222 and the exterior threads 224 (e.g., as depicted by the adapted 220 in FIG. 2A). For another example, if the recessed portion of the prosthetic 100 has a small diameter, the adapter 220 may have no top surface between the inverted frusto-pyramidal portion 222 and the exterior threads 224 (e.g., as depicted by the adapted 220 in FIG. 2B).

The female pyramid 210 may be coupled to the male pyramid 220. The female pyramid 210 comprises an aperture configured to engage the frusto-pyramidal portion 222 of the adapter 220. Preferably, the portion 212 of the adapter 210 is shaped as an inverse inverted frusto-pyramid in order to optimally engage the inverted frusto-pyramidal portion 222 of the adapter 220. A plurality of fasteners 216 (e.g., screws) may then be applied so as to secure the male pyramid 220 to the female pyramid 210. The adapter 210 further comprises an exteriorly threaded portion 214, for example configured to engage the interiorly threaded portion 170 of the socket adapter 160.

The socket adapter 160 may be screwed onto the threads 214 of the adapter 210. Once properly oriented, a fastener, for example a screw through a hole 166 in the adapter 162 or through hole 168 in the adapter 164, may be applied to secure the adapter 160, and thus the socket 150, to the adapter 210. FIG. 2C illustrates an assembled version of the adapter system of FIG. 2A. The prosthetic 100 is mechanically coupled to the adapter 220. The adapter 210 is mechanically coupled to the adapter 220 and fastened by screws 216. The socket adapter 160, which is preferably laminated within a socket 150 (not shown) is mechanically coupled to the adapter 210 and tightened with a screw (not shown) through the hole 166. Additional stability may be provided by gluing the pieces in place (e.g., using epoxy) during or after assembly. It will be appreciated that the mechanical coupling methods described herein may be performed in a different order (e.g., the reverse order) or by adding, deleting, or substituting steps.

Some doctors are very hesitant to amputate far away from certain joints (e.g., knee, ankle), which results in long stumps on users and little space left for connecting mechanical connection units to prosthetic joints, for example connecting the residual limb of a user to an artificial knee or ankle. This can result in incorrect positioning of the center of the prosthetic joint, for example further away from the true knee center, which can cause incorrect gait and user discomfort, such as when the user is sitting down, because the prosthetic knee is further away from the body than the healthy knee. Certain embodiments of the present invention can advantageously reduce the build height of the prosthetic joint, thereby allowing amputation close to certain joints.

Figure 3C:
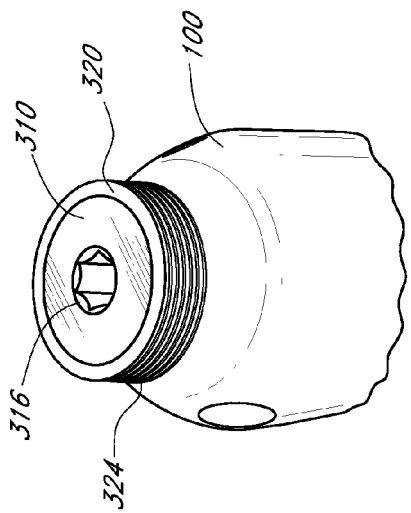
FIG. 3C is a perspective view of further assembly of the elements of FIG. 3A.
Figure 3A:
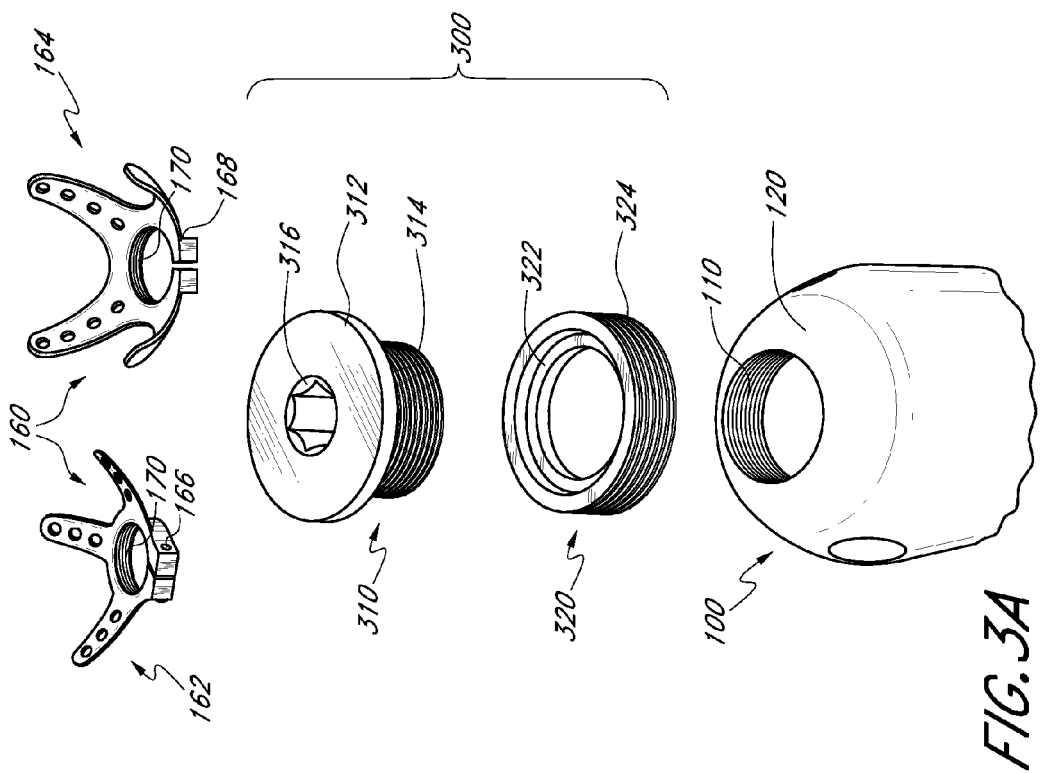
FIG. 3A depicts perspective views of a plurality of adapters that may be used to mechanically couple a prosthetic and a socket with reduced build height.

FIG. 3A depicts perspective views of an embodiment of a system including a plurality of adapters that may be used to mechanically couple the prosthetic 100 and the socket 150 with reduced build height. As described above with reference to FIG. 2A, the socket adapter 160 may comprise a three-prong adapter 162, a four-prong adapter 164, or any suitable adapter.

The system includes a prosthetic 100, a socket adapter 160, and an adapter assembly 300. The prosthetic 100 includes a top surface 120 and an internally threaded surface 110 recessed within the top surface 120. The socket adapter 160 includes an internally threaded surface 170 at a distal end. The adapter assembly 300 has a top end and a bottom end. The adapter assembly 300 comprises a first externally threaded surface 314 configured to operatively engage the internally threaded surface 110 of the prosthetic 100 and a second externally threaded surface 324 configured to operatively engage the internally threaded surface 170 at the distal end of the socket adapter 160. Although illustrated as comprising two pieces, the adapter assembly 300 may also be a single piece or have additional components.

In certain embodiments, an adapter assembly 300 is configured such that the socket adapter 160 extends below the top surface 120 of the prosthetic 100. The adapter assembly 300 may include external threads 324. Other configurations are also possible.

In certain embodiments, the adapter assembly 300 has a height measured between the top and bottom ends is between no more than about 14 and 27.3 mm, preferably between no more than about 14 mm and 22 mm, more preferably between no more than about 14 mm and 18 mm, or even more preferably between no more than about 14 mm and 16 mm Other heights are also possible. In certain embodiments, a height measured between the top surface 120 of the prosthetic 100 and top end of the adapter assembly 300 is between no more than about 6 and 19.3 mm, preferably between no more than about 6 mm and 16 mm, more preferably between no more than about 6 mm and 12 mm, or even more preferably between no more than about 6 mm and 8 mm Other heights are also possible.

In certain embodiments, the second externally threaded surface 324 extends below the top surface 120 of the prosthetic 100 when the adapter assembly 300 is coupled to the prosthetic 100 (see FIG. 3C). In certain embodiments, the distal end of the socket adapter 160 extends below the top surface 120 when the system is assembled (see FIGS. 4A and 4B).

The adapter system 300 for mechanically coupling the prosthetic 100 to the socket 150 illustrated in FIG. 3A comprises two pieces. The first piece, herein referred to as a "male" adapter or element 310, comprises a generally cylindrical main body having a surface including external threads 314, a lip 312 that laterally overlaps the external threads 314 and defines a horizontal lower surface, and a fastening device 316 such as a hexagonal recess. The threaded exterior 314 of the adapter 310 is configured to operatively engage the threaded interior 110 of the prosthetic 100. The second piece, herein referred to as a "female" adapter or element 320, is a generally hollow cylindrical body comprising a surface including exterior threads 324, and may include an internal lip 322 defining a horizontal upper surface. The exterior threads 324 are configured to operatively engage the threaded interior 170 of the adapter 160. The male adapter 310 and female adapter 320 are described in more detail below.

To assemble the system depicted in FIG. 3A, the female adapter 320 is placed on the top 120 of the prosthetic 100. The female adapter 320 has a lower concave surface 326 that preferably matingly engages the domed top surface 120 of the prosthetic 100 (see FIG. 4B). The male adapter 310 is then placed into the female adapter 320 to secure both pieces to the prosthetic 100. Accordingly, the main body of the male adapter 310 is preferably sized to have approximately the same, and slightly smaller, diameter $D_{M2}$ (see FIG. 5E) than the interior diameter $D_{F2}$ (see FIG. 6D) of the female adapter as defined by the internal lip 322. The external threads 314 of the male adapter 310 engage the internal threads 110 of the prosthetic 100, thereby forcing the male adapter 310 towards the prosthetic 100. FIG. 3B illustrates the partially screwed in male adapter 310 surrounded by the female adapter 320 as placed on the prosthetic 100.

When the male adapter 310 reaches a certain depth in the recessed portion of the prosthetic 100, the lip 312 of the male adapter 310 engages the female adapter 320 (e.g., the lip 322 of the female adapter 320), thereby applying pressure to the female adapter 320 and engaging it with the top surface 120 of the prosthetic 100. FIG. 3C illustrates a fully screwed in male adapter 310 engaged with the female adapter 320 and the prosthetic 100, wherein the top surface of the male adapter 310 is preferably flush with the top surface of the female adapter 320. As illustrated, the outer diameter $D_{M1}$ (see FIG. 5D) defined by the lip 312 of the male adapter 310 is preferably approximately the same, and slightly smaller, than the diameter $D_{F1}$ (see FIG. 6D) of the cylindrical inner wall extending from the top surface of the female adapter 320. Although not depicted, the socket adapter 160, which may or may not be laminated within a socket 150, may then be screwed onto the external threads 324 of the female adapter 320, thereby mechanically coupling the socket 150 to the prosthetic 100. The socket adapter 160 may be secured by inserting a fastener (e.g., screw) through the hole 166, 168.

The internal threads 170 of the socket adapter 160 define a socket adapter cavity. In certain embodiments, the male element 310 (or at least the portion of the male adapter extending above the prosthetic 100) is substantially inside the socket adapter cavity when the adapter assembly is coupled to the prosthetic when the system is assembled. In certain embodiments, a substantial portion of the top of the male element 310 engages a top of the socket adapter cavity when the system is assembled. In certain embodiments, the prongs of the socket adapter 160 extend below the top of the male element 310 when the system is assembled.

FIG. 4A shows a side-by-side comparison of the assembled adapter systems described above with respect to FIGS. 2A-2C and 3A-3C. Due to the shape and configuration of the adapters 210, 220 compared to the shape and configuration of the adapters 310, 320, the bottom surface 161 of the socket adapter 162 on the left side is higher from the prosthetic 100 by a distance d than the bottom surface 161 of the socket adapter 162 on the right side. FIG. 4B is a cut-away view of the assemblies of FIG. 4A. On the left side, the male pyramid 220 extends above the top surface 120 of the prosthetic 100, where it is engaged by the female pyramid 210, which then engages the adapter 162. On the right side, the male adapter 310 is inserted into the prosthetic 100, and the female adapter 320, which operatively engages the adapter 162, extends below the top surface 120 of the prosthetic 100. Likewise, the bottom surface of the socket adapter 162 extends below the top surface of the prosthetic 100. As such, a decreased height of distance d may be achieved. The female adapter 320 preferably extends below the top surface 120 of the prosthetic 100, but it will be appreciated that other embodiments wherein the female adapter 320 does not extend below the top surface 120 of the prosthetic 100 may also allow the bottom surface 161 of the adapter 162 to extend below the top surface 120 of the prosthetic 100. In certain embodiments, the bottom surface 161 of the adapter 162 does not extend below the top surface 120 of the prosthetic 100, yet the build height is still less than the build height of the adapter system on the left side. Additional stability may be provided by gluing the pieces in place (e.g., using epoxy) during or after assembly. It will be appreciated that the mechanical coupling methods described herein may be performed in a different order or by adding, deleting, or substituting steps.

FIGS. 5A through 5F illustrate the male adapter 310 in more detail. The male adapter 310 may comprise aluminum, stainless steel, brass, plastic, or any material or combination of materials that can withstand the force applied by a particular user. In some embodiments, the surfaces of the male adapter 310 are coated so as to inhibit corrosion when a metallic male adapter 310 is coupled to adapters comprising different metals.

FIG. 5A is a top perspective top view of the male adapter 310. The male adapter 310 is generally cylindrical in shape, although any shape that can engage the female adapter 310 and the prosthetic 100 may be used. The adapter 310 comprises a surface including an outer surface having external threads 314, a substantially flat upper portion including a lip 312 projecting outwardly from the outer surface, and a fastening device 316. The exterior threads 314 are adapted to operatively engage the internal threads 110 of the prosthetic 100. As depicted, the lip 312 is a disc-shaped, but the lip 312 may be any suitable shape (e.g., comprising one or more protrusions projecting outwardly from the outer surface) that can compress female adapter 320 into the top surface 120 of the prosthetic 100. The fastening device 316 is configured such that a substantially transverse force applied to the fastening device 316 causes rotation of the male adapter 310. As depicted, the fastening device 316 is a hexagonal nut, but the fastening device 316 may be any suitable fastening mechanism that can allow the user to screw the male adapter 310 into the prosthetic 100 (e.g., star nut, four-sided nut, fold-down butterfly nut, Phillips head cross-slot, flat head slot, etc.). Preferably, the fastening device 316 does not extend above the upper surface such that the upper portion is substantially flat.

FIG. 5B is a top schematic perspective view of the male adapter 310.

FIG. 5C is a bottom perspective view of the male adapter 310. As illustrated, the fastening device 316 extends all the way through the adapter 310, although the fastening device 316 may extend only partially through the adapter 310. The threads 314 as illustrated extend substantially close to the lip 312, although it will be appreciated that the threads may only extend as far as necessary for secure fastening of the adapter 310 to the prosthetic 100.

Figure 5F:
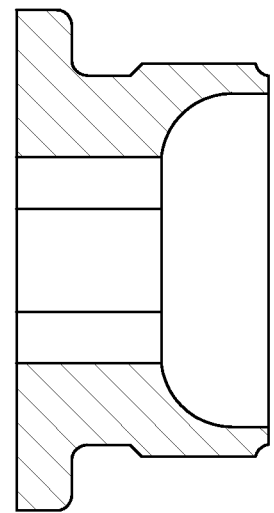
FIG. 5F is a schematic cross-sectional view of the male element of FIG. 5A taken along the line 5F-5F in FIG. 5B.

FIG. 5D is a top plan view of the adapter 310 showing a possible embodiment of a hexagonal nut 316 in more detail. In certain embodiments, the hexagonal nut 316 is sized relative to the size of the male adapter 310 (e.g., the top surface of the male adapter 310). For example, the illustrated hexagonal nut 316 has a width of about 10 mm and the top surface of the male adapter 310 has a diameter $D_{M1}$ (see FIG. 5F) of about 28 mm.

Figure 5E:
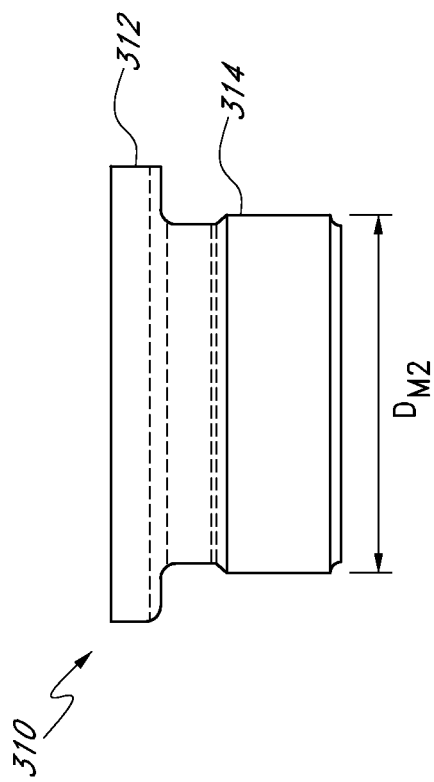
FIG. 5E is a schematic side plan view of the male element of FIG. 5A.

FIG. 5E is a side schematic view of the adapter 310, which illustrates further example measurements of particular components of certain embodiments. For example, the threads 314 may be M22×1.0-4 h type. Other threads types are also possible depending on the specific manufacture of the prosthetic 100 (e.g., having a wider pitch). For another example, the lip 312 may extend beyond the external threads 314 by about 3.5 mm on each side. For yet another example, the adapter 310 of FIG. 5C has an approximately 4 mm "neck" between the external threads 314 and the lip 312. Other dimensions may be suitable for various prosthetics 100 and female adapters 320.

FIG. 5F is a cross-sectional view of the adapter 310 taken along line 5F-5F of FIG. 5B. The interior of the male adapter 310 may comprise a wide variety of shapes. For example, as illustrated in FIG. 5F, the male adapter has a hollowed interior lower portion with rounded walls of radius 4 mm. A wide variety of modifications can be made, for example, to engage or avoid certain components within the recessed portion of the prosthetic 100, as long as the male adapter 310 is able to operatively engage the threads 110 of the prosthetic 100 and to engage the female adapter 320.

FIGS. 6A through 6F illustrate the female adapter 320 in more detail. The female adapter 320 may comprise aluminum, stainless steel, brass, plastic, or any material or combination of materials that can withstand the force applied by a particular user. In some embodiments, the surfaces of the female adapter 320 are coated so as to inhibit corrosion when a metallic female adapter 320 is coupled to adapters comprising different metals.

Figure 6B:
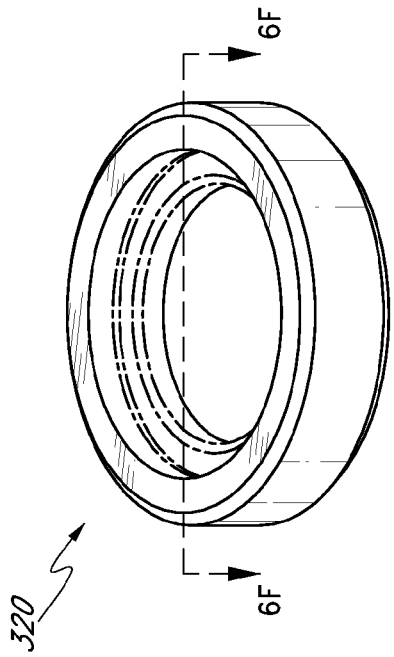
FIG. 6B is a schematic top perspective view of the female element of FIG. 6A.
Figure 6D:
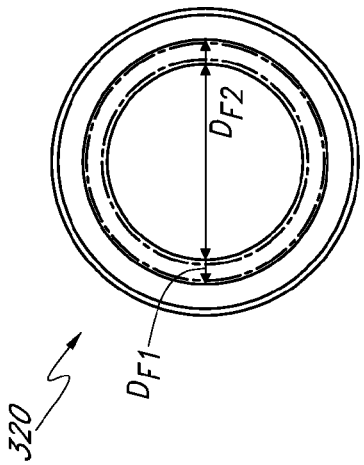
FIG. 6D is a schematic top plan view of the female element of FIG. 6A.
Figure 6A:
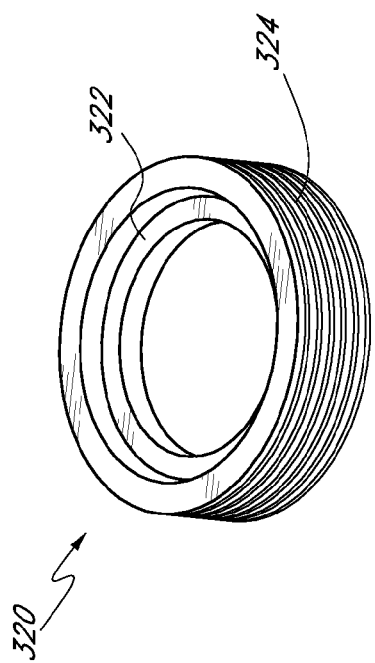
FIG. 6A is a top perspective view of a female element of an example adapter.

FIG. 6A is a top perspective top view of the female adapter 320. The female adapter 320 is generally hollow and generally cylindrical, although any shape that can engage the male adapter 320 and the socket adapter 160 may be used. The adapter 320 comprises an outer surface having exterior threads 324, an upper portion including a lip 322 projecting inwardly from an interior surface, and a lower portion including a rounded surface 326 (see FIG. 6B). The exterior threads 324 are adapted to operatively engage the internal threads 170 of the socket adapter 160. In the embodiment illustrated in FIG. 6A, the adapter 320 comprises a ring-shaped lip 322 extending laterally inward from the external threads 324. In embodiments including a lip 322, the lip 322 may be any suitable shape (e.g., comprising one or more protrusions extending laterally inward from the threaded portion 324) that can engage the lip 312 of the male adapter 310 such that the female adapter 320 is compressed into the top surface 120 of the prosthetic 100 when the male adapter 310 is screwed into the prosthetic 100. In embodiments not including a lip 322, the lip 312 of the male adapter 310 may apply pressure to the top surface of the female adapter 320. For example, see FIG. 9A. The threads 324 as illustrated extend substantially across the exterior surface of the female adapter 320, although it will be appreciated that the threads may only extend as far as necessary for secure fastening of the adapter 160 to the adapter 320. FIG. 6B is a top schematic perspective view of the female adapter 320.

Figure 6C:
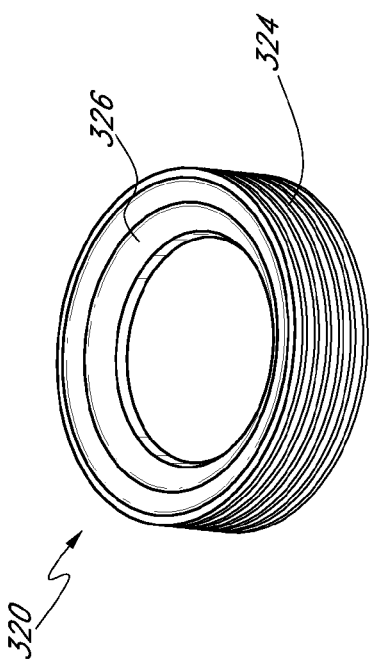
FIG. 6C is a bottom perspective view of the female element of FIG. 6A.

FIG. 6C is a bottom perspective view of the female adapter 320. In the illustrated embodiment, the adapter 320 has a bottom portion 326 that is concavely shaped so as to conformally engage a domed top surface 120 of a prosthetic 100. Such shaping may help to prevent scratching of the top surface 120 of the prosthetic 100 and to provide increased surface area to engage the prosthetic 100. In some embodiments, the bottom portion 326 of the adapter 320 is shaped so as to engage the top surface 120 of the prosthetic 100 at a plurality of points or to avoid contacting the prosthetic 100.

FIG. 6D is a top schematic view of the female adapter 320. The adapter 320 has an interior diameter $D_{F1}$ that is larger than the outer diameter $D_{M1}$ of the male adapter 310 illustrated in FIG. 5D such that adapters 310, 320 form a flat surface when joined, as illustrated in FIG. 3C. The adapter 320 has an interior diameter $D_{F2}$ that is larger than the outer diameter $D_{M2}$ of the male adapter 310 illustrated in FIG. 5E such that adapter 310 may extend through the adapter 320.

FIG. 6E is a side schematic view of the adapter 320, which illustrates example measurements of particular components of certain embodiments. For example, the threads 324 may be M36×1.5–6 g type. Other threads types are also possible depending on the manufacture of the socket adapter 160 (e.g., having a wider pitch). Other dimensions may be suitable for various prosthetics 100 and female adapters 320.

FIG. 6F is a cross-sectional view of the adapter 320 taken along line 6F-6F of FIG. 6B, which illustrates further example measurements of particular components of certain embodiments. For example, the interior diameter $D_{F1}$ may be about 28.2 mm when the outer diameter $D_{M1}$ is about 28 mm. A wide variety of modifications can be made as long as the female adapter 320 is able to operatively engage the threads 170 of the adapter 160 and operatively engage the male adapter 310.

Figure 7B:
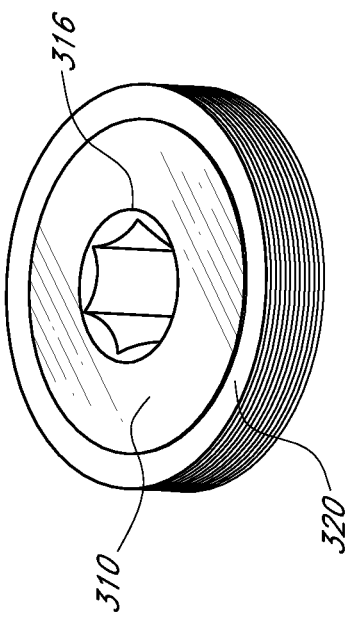
FIG. 7B is a top perspective view of the coupled adapter of FIG. 7A.
Figure 7A:
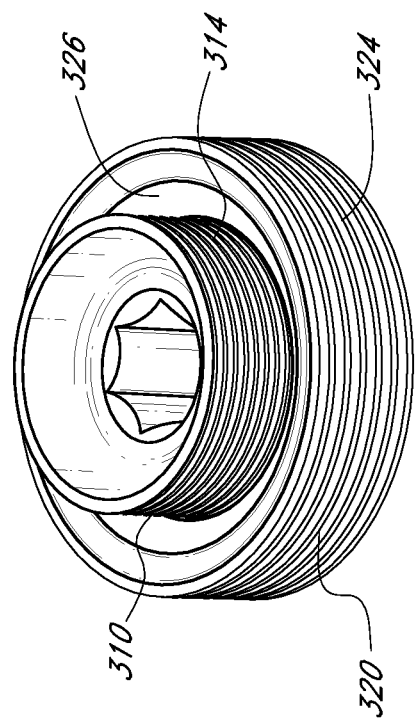
FIG. 7A is a bottom perspective view of the male and female elements of FIGS. 5A and 6A coupled together.

FIG. 7A is a bottom perspective view of the adapters 310 and 320 coupled together. Looking at the joined adapters 310, 320 from the bottom, the bottom rounded surface 326 of the female adapter 320, and the threaded portions 314, 324 are exposed. FIG. 7B illustrates a top perspective view of the adapters 310 and 320 coupled together. Looking at the joined adapters 310, 320 from the top, the connector 316 and the flat top surfaces of the adapters 310, 320 are exposed.

As described above, the threaded portions 314, 324 on the surfaces of the adapters 310, 320 may extend for only a portion of their respective external surfaces. FIG. 8A illustrates an embodiment in which the threads 324 of the adapter 320 extend substantially the entire height of the outer surface of the adapter 320. The exterior threads 312 of the adapter 310 extend for a length that is similar to the depth of the recess of the prosthetic 100. Given the shapes of the particular adapters 310, 320, in this embodiment, the threads 324 overlap the threads 312 by a distance o when the adapters 310, 320 are coupled. FIG. 8B illustrates an embodiment in which the threads 324 of the adapter 320 extend only partially across the exterior surface of the adapter 320 and in which the threads 312 of the adapter 310 extend only for a portion of the depth of the recess of the prosthetic 100. In such an embodiment, the threads are separated by a distance s when the adapters 310, 320 are coupled. FIG. 8C illustrates another embodiment in which the threads 324 of the adapter 320 extend substantially the entire height of the outer surface of the adapter 320 and in which the threads 312 of the adapter 310 extend only for a portion of the depth of the recess of the prosthetic 100. In such an embodiment, the threads are separated by a distance s when the adapters 310, 320 are coupled. A wide variety of threading configurations are possible, as long as the male adapter 310 can securely engage the prosthetic 100 and as long as the female adapter 320 can securely engage the adapter 160.

FIGS. 9A through 9D illustrate alternative embodiments of adapter systems that may be used to couple the prosthetic 100 to the adapter 160. FIG. 9A illustrates an embodiment in which a female adapter 320 does not have a recessed portion or a lip 322. In the illustrated embodiment, the male adapter 310 has a lip 312 that extends over the top surface 328 of the adapter 320 (e.g., substantially to the outer surface of the adapter 320). Thus, when the male adapter 310 is screwed into the prosthetic 100, the lip 312 compresses the top surface 328 of the female adapter 320 to the top surface 120 of the prosthetic 100. In such an embodiment, the build height of the adapter system may be similar to the adapter system illustrated in FIG. 3A by decreasing the height of the female adapter 320. If the height of the adapter 320 is not sufficient to engage the adapter 160, adjustments can be made, for example, by adding threading similar to the threads 324 the exterior of the lip 312.

The preferred embodiment of a reduced build height adapter system comprises two pieces because independent pieces allows, for example, one piece (e.g., a female adapter 320) to balance abnormal stresses applied by the another piece (e.g., a male adapter 310), to align to the top surface 120 of the prosthetic 100, to decrease scratching of the top surface 120 of the prosthetic 100, and to maintain strength due to increased surface contact with the top surface 120 of the prosthetic 100. However, embodiments comprising one piece are also possible. FIG. 9B illustrates an embodiment in which the male adapter 310 and female adapter 320 are formed as a single adapter 330. The adapter 330 looks substantially like the joined male and female adapters illustrated in FIGS. 7A and 7B. The single adapter 330 has exterior threads 332, exterior threads 334, and a surface to engage the top surface 120 of the prosthetic 100.

FIG. 9C illustrates an embodiment of a one piece adapter 340 that is shaped so as to not contact the top surface 120 of the prosthetic 100. The adapter 340 comprises external threads 342 and external threads 344. Such an embodiment may advantageously prevent scratching of the top surface of the prosthetic 100, although an appropriate material should be selected such that the strength and structural integrity of the adapter system is maintained. For example, in some embodiments, the external threads 342 extend the same height as the external threads 332 of FIG. 9B or the external threads 324 of FIG. 8A in order to provide a large surface for engagement of the threads 170 of the adapter 160.

FIG. 9D illustrates an embodiment in which a female adapter 360 includes an inverted frusto-pyramid and in which a male adapter 350 includes a male frusto-pyramid. The male adapter 350 is screwed into the prosthetic 100. The female adapter 360 is then secured to the male adapter 350 by applying a plurality of fasteners 370 (e.g., screws), which also couples the bottom surface of the female adapter 360 to the top surface 120 of the prosthetic 100. The socket adapter 160 may then be screwed onto the external threads 362 of the female adapter 360. In such an embodiment, the build height of the adapter system may be similar to the adapter system illustrated in FIG. 3A by decreasing the height of the female adapter 320 as compared to the female pyramid 210. Unlike the female pyramid 210, in which the fasteners 216 extend through a portion that is spaced from the externally threaded surface 214, the fasteners 370 extend through a portion of adapter 360 that is externally threaded. Preferably, four fasteners 370 are engaged for a four-sided frusto-pyramid, which leaves enough surface area for the adapter 160 to operatively engage the external threads 362 of the adapter 360.

FIG. 10A illustrates a variety of prosthetics that may be coupled to sockets. The prosthetic 1010 is a Flex-Foot® Axia™, available from Össur. The prosthetic 1020 is a Proprio Foot™, also available from Össur. The prosthetic 1030 is a Rheo Knee™, also available from Össur. Prosthetics from other manufacturers are also possible. In preferred embodiments, the prosthetic 100 has a domed top surface 120, such as illustrated by each of the prosthetics 1010, 1020, 1030. Although the prosthetics 1010, 1020, 1030 have an inverted pyramid insert, each prosthetic 1010, 1020, 1030 also has a recess comprising interior threads 110 similar to the prosthetic 100 (not shown). Thus, it will be appreciated that the methods and apparatuses described herein may also be suitable for a wide variety of prosthetics having a recess including internal threads.

Figure 10B:
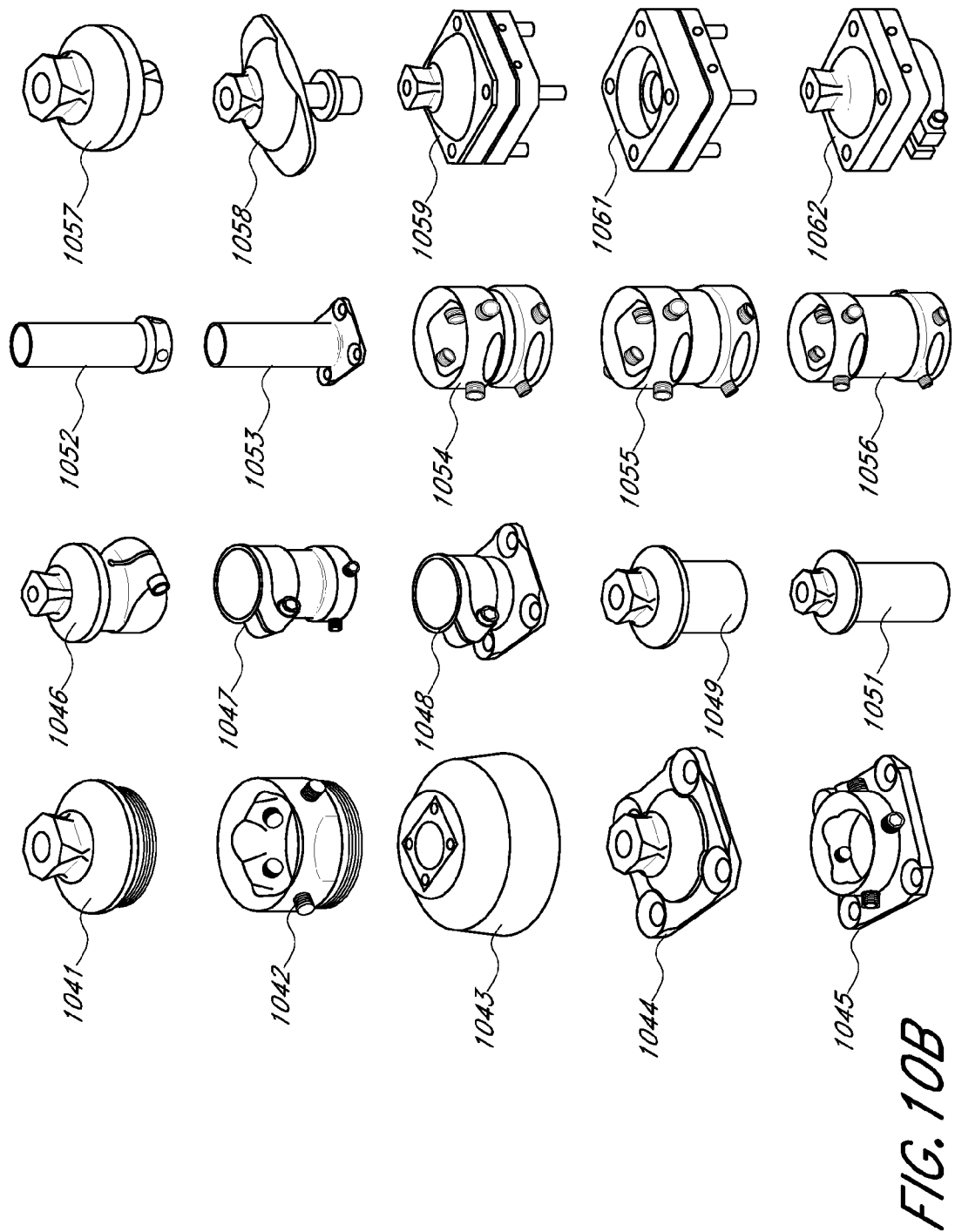
FIG. 10B is a perspective view of a plurality of example adapters.

FIG. 10B illustrates a variety of adapters that the adapter systems described herein may be used in conjunction with or instead of. The adapter 1041 is a male pyramid insert (e.g., similar to the adapter 220 described above). The adapter 1042 is a female pyramid insert (e.g., similar to the adapter 210 described above). The adapter 1043 is a socket attachment block. The adapter 1044 is a 4-hole male pyramid. The adapter 1045 is a 4-hole female pyramid. The adapter 1046 is a male pyramid tube clamp. The adapter 1047 is a female pyramid tube clamp. The adapter 1048 is a 4-hole tube clamp. The adapter 1049 is a male single adapter, short. The adapter 1051 is a male single adapter, long. The adapter 1052 is a female single adapter. The adapter 1053 is a 4-hole single adapter. The adapter 1054 is a 32 mm female double adapter. The adapter 1055 is a 45 mm double female adapter. The adapter 1056 is a 60 mm female double adapter. Other double female adapter lengths are also possible (e.g., 75 mm) The adapter 1057 is a male double adapter. The adapter 1058 is a sach foot adapter. The adapter 1059 is a slide adapter euro 4-hole with male pyramid. The adapter 1061 is a slide adapter euro 4-hole. The adapter 1062 is a male pyramid slide adapter M36×1.5–6 g thread. It will be appreciated that the embodiments described herein may also be used instead of or in addition to other types of adapters for prosthetics.

FIGS. 11A-11C illustrate an example embodiment of an adapter 1100 compatible with the adapter systems described herein: FIG. 11A is a top perspective view; FIG. 11B is a bottom perspective view; and FIG. 11C is a top plan view. The adapter 1100 comprises a tube having a bore therethrough. The tube includes a slot 1102, which allows the tube to have a reduced interior volume when laterally compressed, for example by a fastener inserted through the fastener bore 1104. As illustrated in FIG. 11B, the adapter 1100 includes a bottom surface 1106 adapted to engage the top surface 120 of a prosthetic 100. In the illustrated embodiment, the adapter 1100 has a bottom surface 1106 that is concavely shaped so as to conformally engage a domed top surface 120 of a prosthetic 100. Such shaping may help to prevent scratching of the top surface 120 of the prosthetic 100 and to provide increased surface area to engage the prosthetic 100. In some embodiments, the bottom surface 1106 of the adapter 1100 is shaped so as to engage the top surface 120 of the prosthetic 100 at a plurality of points or to avoid contacting the prosthetic 100. As illustrated in FIG. 11C, the adapter 1100 includes a shoulder 1108 adapted to engage the lip 312 of a male adapter 310. In the embodiment illustrated in FIG. 11C, the adapter 1100 comprises a ring-shaped shoulder 1108 extending laterally inward from the tube. In some embodiments, the shoulder is shaped to allow a tube connector or "pylon" (e.g., the adapter 1051 illustrated in FIG. 10B) inserted into the tube to extend below the shoulder 1108 (e.g., around the shoulder 1108 and a male adapter 310). In embodiments including a shoulder 1108, the shoulder 1108 may be any suitable shape (e.g., comprising one or more protrusions extending laterally inward from the threaded portion 324) that can engage the lip 312 of the male adapter 310 such that the adapter 1100 is compressed into the top surface 120 of the prosthetic 100 when the male adapter 310 is screwed into the prosthetic 100. Accordingly, the adapter 1100 may be considered a "female" adapter or element. In certain embodiments, the shoulder 1108 is disposed proximate to and on an opposite side of the bottom surface 1106 such that the shoulder 1108 resides at a low position within the tube, thereby allowing for a low build height. As the position of the shoulder 1108 within the tube increases, the minimum build height of a system comprising the adapter 1100 increases.

FIG. 11D schematically illustrates an example adapter system that may be used to mechanically couple the prosthetic 100 to a tube connector (e.g., the adapter 1051 illustrated in FIG. 10B). To assemble the system depicted in FIG. 11D, the adapter 1100 is placed on the top 120 of the prosthetic 100. The adapter 1100 has a lower concave surface 1106 that preferably matingly engages the domed top surface 120 of the prosthetic 100. The male adapter 310 is then placed into the adapter 1100 to secure both pieces to the prosthetic 100. Accordingly, the main body of the male adapter 310 is preferably sized to have approximately the same, and slightly smaller, diameter $D_{M2}$ than the interior diameter of the adapter 1100. The external threads 314 of the male adapter 310 engage the internal threads 110 of the prosthetic 100, thereby forcing the male adapter 310 towards the prosthetic 100. When the male adapter 310 reaches a certain depth in the recessed portion of the prosthetic 100, the lip 312 of the male adapter 310 engages the adapter 1100 (e.g., the shoulder 1108 of the adapter 1100), thereby applying pressure to the adapter 1100 and engaging it with the top surface 120 of the prosthetic 100. When assembled, the adapter 1100 extends below the top surface 120 of the prosthetic 100, and a pylon (e.g., the adapter 1051) may project further towards the prosthetic 100 (e.g., until contact with the adapter 310) than in systems in which the adapter does not extend below the top surface 120 of the prosthetic 100, thereby providing a lower build height of the adapter assembly.

Figure 12C:
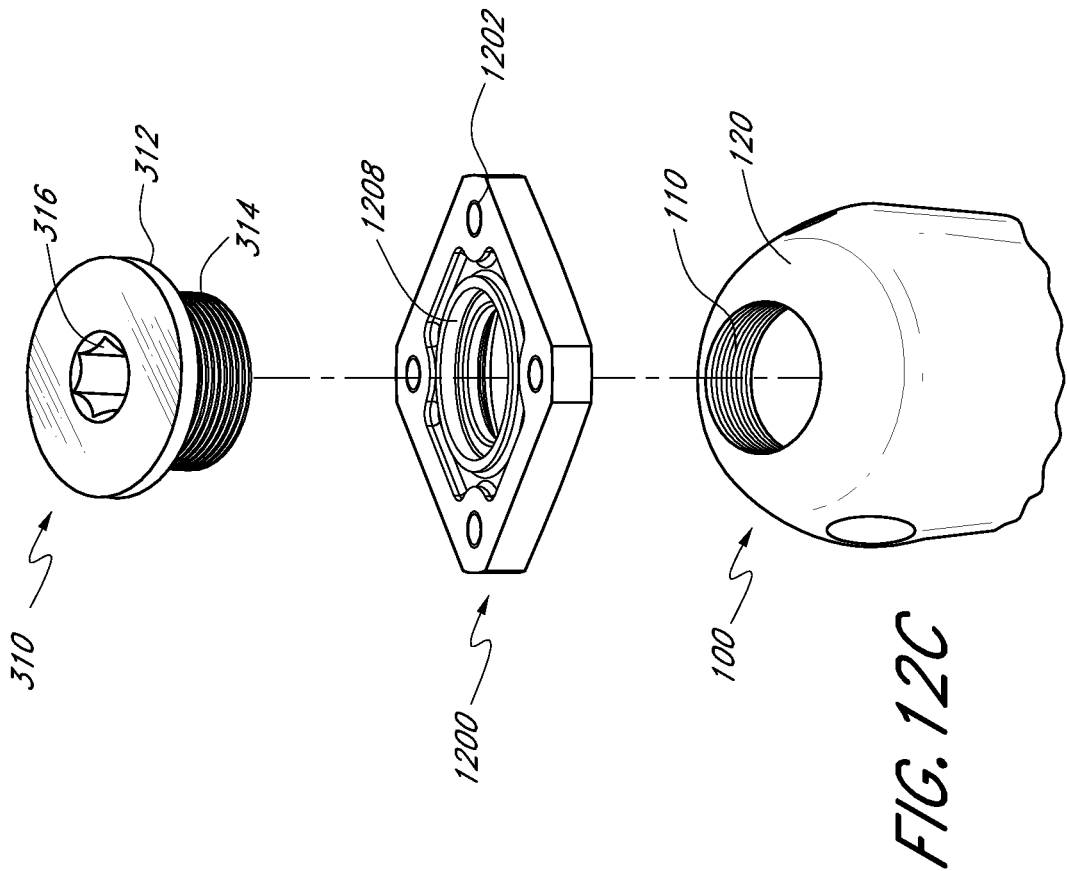
FIG. 12C is a perspective view of partial assembly of the female element of FIG. 12A with the male element of FIG. 5A and the prosthetic of FIG. 1A.
Figure 12A:
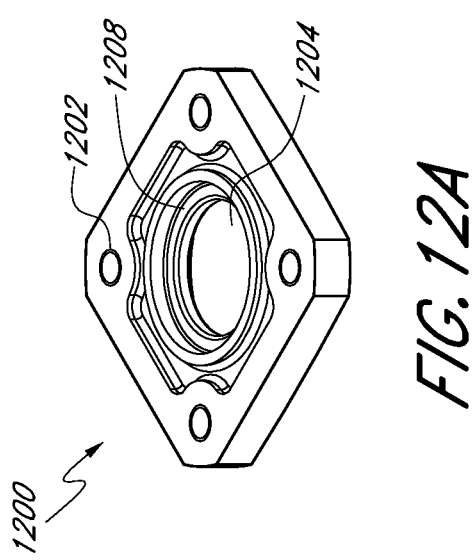
FIG. 12A is a top perspective view of another female element of an example adapter.
Figure 12B:
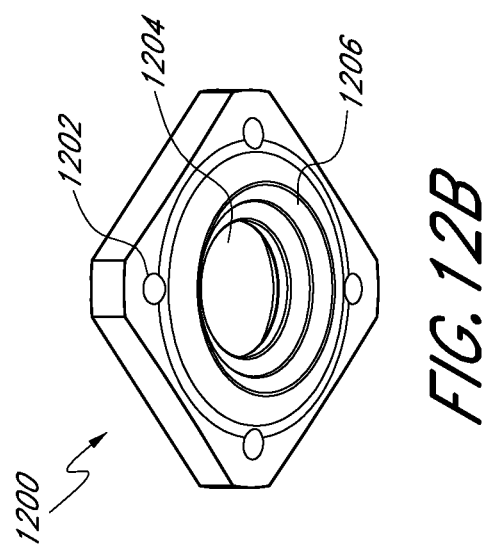
FIG. 12B is a bottom perspective view of the female element of FIG. 12A.

FIGS. 12A and 12B illustrate another example embodiment of an adapter 1200 compatible with the adapter systems described herein: FIG. 12A is a top perspective view and FIG. 12B is a bottom perspective view. The adapter 1200 comprises a plate having a bore 1204 therethrough. The plate includes a plurality of fastener bores 1202, which allow the plate to be secured to an adapter (e.g., one of the adapters 1045, 1048, 1059, 1061 illustrated in FIG. 10B). As illustrated in FIG. 12A, the adapter 1200 includes a shoulder 1208 adapted to engage the lip 312 of a male adapter 310. In the embodiment illustrated in FIG. 12A, the adapter 1200 comprises a ring-shaped shoulder 1208 extending laterally inward from the tube. In embodiments including a shoulder 1208, the shoulder 1208 may be any suitable shape (e.g., comprising one or more protrusions extending laterally inward from the threaded portion 324) that can engage the lip 312 of the male adapter 310 such that the adapter 1200 is compressed into the top surface 120 of the prosthetic 100 when the male adapter 310 is screwed into the prosthetic 100. As illustrated in FIG. 12B, the adapter 1200 includes a bottom surface 1206 adapted to engage the top surface 120 of a prosthetic 100. In the illustrated embodiment, the adapter 1200 has a bottom surface 1206 that is concavely shaped so as to conformally engage a domed top surface 120 of a prosthetic 100. Such shaping may help to prevent scratching of the top surface 120 of the prosthetic 100 and to provide increased surface area to engage the prosthetic 100. In some embodiments, the bottom surface 1206 of the adapter 1200 is shaped so as to engage the top surface 120 of the prosthetic 100 at a plurality of points or to avoid contacting the prosthetic 100. Accordingly, the adapter 1200 may be considered a "female" adapter or element.

FIG. 12C schematically illustrates an example adapter system that may be used to mechanically couple the prosthetic 100 to an adapter (e.g., one of the adapters 1044, 1045, 1048, 1053, 1059, 1061 illustrated in FIG. 10B). To assemble the system depicted in FIG. 12C, the adapter 1200 is placed on the top 120 of the prosthetic 100. The adapter 1200 has a lower concave surface 1206 that preferably matingly engages the domed top surface 120 of the prosthetic 100. The male adapter 310 is then placed into the adapter 1200 to secure both pieces to the prosthetic 100. The external threads 314 of the male adapter 310 engage the internal threads 110 of the prosthetic 100, thereby forcing the male adapter 310 towards the prosthetic 100. When the male adapter 310 reaches a certain depth in the recessed portion of the prosthetic 100, the lip 312 of the male adapter 310 engages the adapter 1200 (e.g., the shoulder 1208 of the adapter 1200), thereby applying pressure to the adapter 1200 and engaging it with the top surface 120 of the prosthetic 100.

Figure 13C:
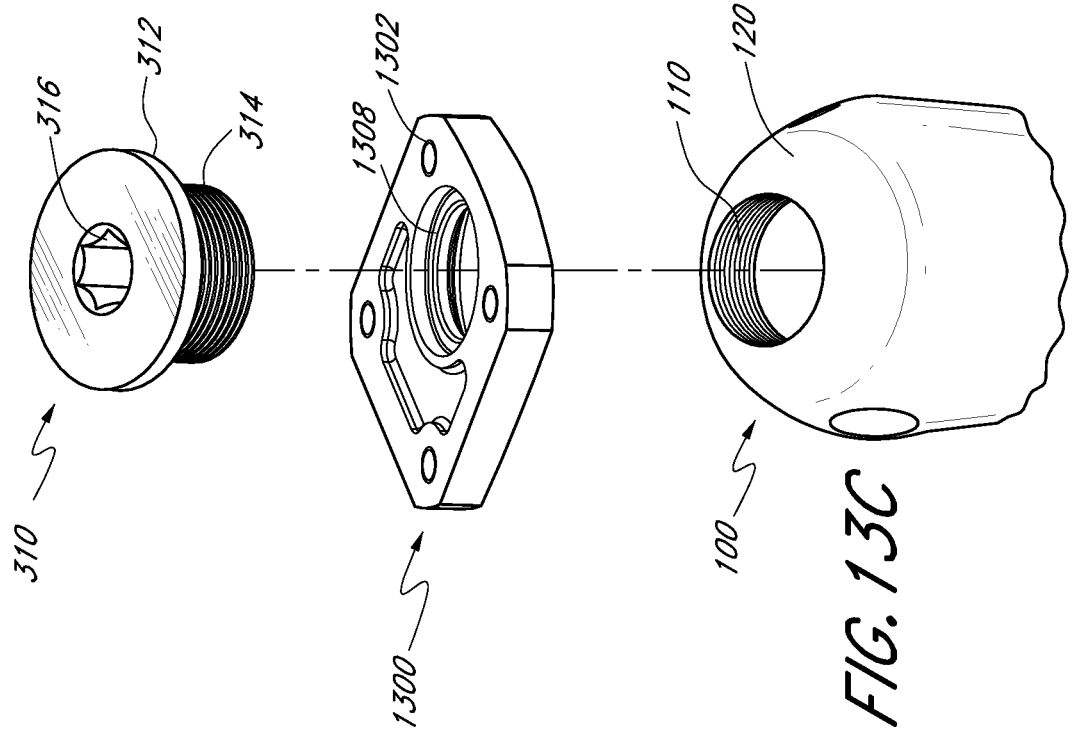
FIG. 13C is a perspective view of partial assembly of the female element of FIG. 13A with the male element of FIG. 5A and the prosthetic of FIG. 1A.
Figure 13A:
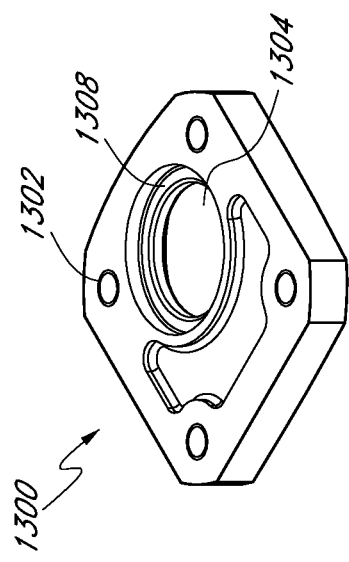
FIG. 13A is a top perspective view of another female element of an example adapter.
Figure 13B:
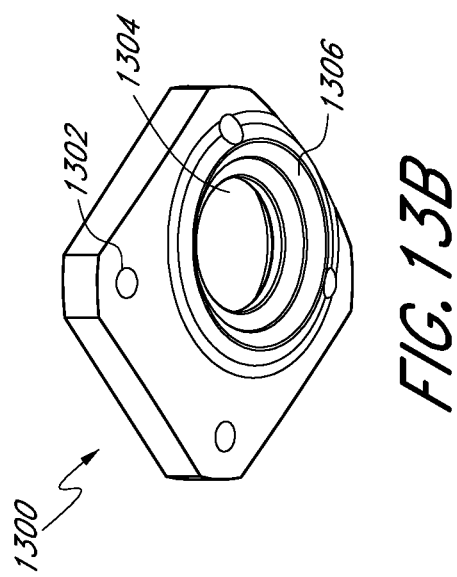
FIG. 13B is a bottom perspective view of the female element of FIG. 13A.

FIGS. 13A and 13B illustrate yet another example embodiment of an adapter 1300 compatible with the adapter systems described herein: FIG. 13A is a top perspective view and FIG. 13B is a bottom perspective view. The adapter 1300 comprises a plate having a bore 1304 therethrough. The bore 1304 is shifted from the center of the plate (e.g., by about 9 mm). The plate includes a plurality of fastener bores 1302, which allow the plate to be secured to an adapter (e.g., one of the adapters 1044, 1045, 1048, 1053, 1059, 1061 illustrated in FIG. 10B). As illustrated in FIG. 13A, the adapter 1300 includes a shoulder 1308 adapted to engage the lip 312 of a male adapter 310. In the embodiment illustrated in FIG. 13A, the adapter 1300 comprises a ring-shaped shoulder 1308 extending laterally inward from the tube. In embodiments including a shoulder 1308, the shoulder 1308 may be any suitable shape (e.g., comprising one or more protrusions extending laterally inward from the threaded portion 324) that can engage the lip 312 of the male adapter 310 such that the adapter 1300 is compressed into the top surface 120 of the prosthetic 100 when the male adapter 310 is screwed into the prosthetic 100. As illustrated in FIG. 13B, the adapter 1300 includes a bottom surface 1306 adapted to engage the top surface 120 of a prosthetic 100. In the illustrated embodiment, the adapter 1300 has a bottom surface 1306 that is concavely shaped so as to conformally engage a domed top surface 120 of a prosthetic 100. Such shaping may help to prevent scratching of the top surface 120 of the prosthetic 100 and to provide increased surface area to engage the prosthetic 100. In some embodiments, the bottom surface 1306 of the adapter 1300 is shaped so as to engage the top surface 120 of the prosthetic 100 at a plurality of points or to avoid contacting the prosthetic 100. Accordingly, the adapter 1300 may be considered a "female" adapter or element.

FIG. 13C schematically illustrates an example adapter system that may be used to mechanically couple the prosthetic 100 to an adapter (e.g., one of the adapters 1045, 1048, 1059, 1061 illustrated in FIG. 10B). To assemble the system depicted in FIG. 13C, the adapter 1300 is placed on the top 120 of the prosthetic 100. The adapter 1300 has a lower concave surface 1306 that preferably matingly engages the domed top surface 120 of the prosthetic 100. The male adapter 310 is then placed into the adapter 1300 to secure both pieces to the prosthetic 100. The external threads 314 of the male adapter 310 engage the internal threads 110 of the prosthetic 100, thereby forcing the male adapter 310 towards the prosthetic 100. When the male adapter 310 reaches a certain depth in the recessed portion of the prosthetic 100, the lip 312 of the male adapter 310 engages the adapter 1300 (e.g., the shoulder 1308 of the adapter 1300), thereby applying pressure to the adapter 1300 and engaging it with the top surface 120 of the prosthetic 100.

The embodiments described above explain screwing the adapter 160 onto the adapters 320 et al. by rotation such that the socket 150 is fixed in the sagittal plane and the coronal plane but can be rotated in the transverse plane. In alternative embodiments, the adapter 160 and the adapters 320 et al. may be modified so as to not limit the rotation in the transverse plane but to enable angular alignment (e.g., a few degrees of angular alignment) in both the sagittal plane and the coronal plane.

Certain embodiments of the present invention can lower the build height by approximately 13.4 mm, thus allowing the possibility to move the center of the prosthetic joint closer to the true anatomical center of the joint than with previous systems. Certain embodiments of the present invention may also minimize the minimum distance from the center of the prosthetic joint to a user's residual limb, thus making it possible for users with long residual limbs and residual limbs which have been amputated too close to the joint to use prosthetic joints (e.g., Rheo Knee™, Proprio Foot™) with domed tops and making it possible to have the prosthetic joint center close to true anatomical joint center.

While certain embodiments of the inventions have been described, these embodiments have been presented by way of example only, and are not intended to limit the scope of the inventions. Indeed, the novel methods and systems described herein may be embodied in a variety of other forms. For example, the foregoing may be applied to the motion-control of joints other than the knee, such as an ankle or a shoulder. Furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while several variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. A method of mechanically coupling a prosthetic and a socket adapter using an adapter assembly, wherein the socket adapter is attachable to a socket configured to fit around a residual limb, the method comprising:
   extending a male element of the adapter assembly through a bore of a female element of the adapter assembly, the male element comprising exterior threads and a lip projecting outwardly from an outer surface, and the female element comprising the bore therethrough and a shoulder projecting inwardly from an inner surface of the bore;
   engaging the exterior threads of the male element to an internally threaded surface recessed within a top surface of the prosthetic; and
   engaging the female element to the socket adapter, wherein the lip of the male element engages the shoulder of the female element to secure the prosthetic to the socket adapter.

2. The method of claim 1, wherein a distal end of the socket adapter extends below the top surface of the prosthetic when assembled.

3. The method of claim 1, wherein the female element extends below the top surface of the prosthetic when assembled.

4. The method of claim 1, wherein the female element comprises an externally threaded surface configured to engage an internally threaded surface proximate to a distal end of the socket adapter.

5. The method of claim 1, wherein the female element contacts the prosthetic when assembled.

6. The method of claim 1, further comprising adhering the male and female elements together.

7. A method comprising mechanically coupling a prosthetic limb and a socket adapter attachable to a socket configured to fit around a residual limb via an adapter assembly having an externally threaded surface that extends over substantially an entire height of an outer surface of the adapter assembly extending from a top surface of the prosthetic limb when coupled thereto, the socket adapter defined by a single piece including a base having a internally threaded surface and a plurality of prongs extending from the base, the plurality of prongs configured to attach to the socket, wherein, after coupling of the prosthetic limb with the socket adapter via the adapter assembly by engaging the externally threaded surface of the adapter assembly with the internally threaded surface of the socket adapter, a bottom surface of the socket adapter is disposed about an upper end of the prosthetic limb and fixed below a top surface of the prosthetic limb such that the socket adapter extends over the externally threaded surface of the adapter assembly that extends from the top surface of the prosthetic limb.

8. The method of claim 7, wherein coupling comprises operatively engaging an adapter assembly to the prosthetic and the socket adapter such that at least a portion of the adapter assembly extends into a recessed portion of the prosthetic and into the base of the socket adapter.

9. The method of claim 8, wherein the adapter assembly comprises a plurality of components.

10. The method of claim 7, wherein coupling comprises operatively engaging a second externally threaded surface of the adapter assembly with an internally threaded surface of the prosthetic limb and operatively engaging the externally threaded surface of the adapter assembly with the first internally threaded surface of the socket adapter.

11. The method of claim 10, wherein, after coupling, the first externally threaded surface extends below the top surface of the prosthetic.

12. The method of claim 11, wherein, after coupling, the second externally threaded surface extends below the top surface of the prosthetic.

13. A method of mechanically coupling a prosthetic limb having a top surface and a socket adapter, the socket adapter defined by a single piece including a base and a plurality of prongs extending from the base, the plurality of prongs configured to attach to a socket configured to fit around a residual limb, the method comprising:
   coupling an adapter assembly having an externally threaded surface that extends from a top surface of the prosthetic limb when coupled thereto to the prosthetic limb and to the base of the socket adapter by engaging the externally threaded surface of the adapter assembly to an internally threaded surface in the base of the socket adapter such that a bottom surface of the socket adapter is disposed about an upper end of the prosthetic and extends below the top surface of the prosthetic, wherein the externally threaded surface extends over substantially an entire height of an outer surface of the adapter assembly extending from the top surface of the prosthetic limb.

14. The method of claim 13, wherein coupling the adapter assembly to the prosthetic and the socket adapter further comprises:
   engaging a second externally threaded surface of the adapter assembly to an internally threaded surface recessed within the top surface of the prosthetic limb.

15. The method of claim 14, wherein the second externally threaded surface extends below the top surface of the prosthetic when the adapter assembly is coupled to the prosthetic.

16. The method of claim 14, wherein the adapter assembly comprises a plurality of components.

17. The method of claim 16, further comprising engaging a first of the plurality of components to a second of the plurality of components.

18. The method of claim 16, further comprising adhering the plurality of components together.

19. The method of claim 16, wherein the adapter assembly comprises a male element comprising the first externally threaded surface and a female element comprising the second externally threaded surface, the method further comprising engaging the male element to the female element.

20. The method of claim 19, further comprising engaging the male element to the female element so that the female element contacts the top surface of the prosthetic.

21. The method of claim 7, wherein coupling comprises operatively engaging an externally threaded surface of the adapter assembly with the internally threaded surface of the socket adapter.

22. The method of claim 13, wherein coupling the adapter assembly to the prosthetic and the socket adapter comprises engaging an externally threaded surface of the adapter assembly to an internally threaded surface in the base of the socket adapter.

* * * * *

UNITED STATES PATENT AND TRADEMARK OFFICE
CERTIFICATE OF CORRECTION

PATENT NO.        : 8,992,630 B2
APPLICATION NO.   : 13/480193
DATED             : March 31, 2015
INVENTOR(S)       : Sigurdur Olafsson and Helgi Jonsson Page 1 of 1

It is certified that error appears in the above-identified patent and that said Letters Patent is hereby corrected as shown below:

On the Title Page
In page 1, item 62, line 2, change "PCT/US2007/007855" to --PCT/US2007/078558--.
In the Specification
In column 8, line 1, change "16 mm" to --16 mm.--.
In column 8, line 8, change "8 mm" to --8 mm.--.
In the Claims
In column 18, line 12, in claim 10, after "the" delete "first".

Signed and Sealed this
Tenth Day of May, 2016

Michelle K. Lee
*Director of the United States Patent and Trademark Office*